(12) United States Patent
Lee et al.

(10) Patent No.: US 9,238,629 B2
(45) Date of Patent: Jan. 19, 2016

(54) HETEROARYL COMPOUNDS AND USES THEREOF

(75) Inventors: Kwangho Lee, Waltham, MA (US); Deqiang Niu, Lexington, MA (US); Russell C. Petter, Stow, MA (US); Juswinder Singh, Ashland, MA (US)

(73) Assignee: Celgene Avilomics Research, Inc., Bedford, MA (US)

( * ) Notice: Subject to any disclaimer, the term of this patent is extended or adjusted under 35 U.S.C. 154(b) by 299 days.

(21) Appl. No.: 13/286,062

(22) Filed: Oct. 31, 2011

(65) Prior Publication Data

US 2012/0149722 A1 Jun. 14, 2012

Related U.S. Application Data

(60) Provisional application No. 61/409,074, filed on Nov. 1, 2010, provisional application No. 61/411,834, filed on Nov. 9, 2010, provisional application No. 61/412,324, filed on Nov. 10, 2010, provisional application No. 61/534,306, filed on Sep. 13, 2011.

(51) Int. Cl.
*A61K 31/505* (2006.01)
*C07D 239/48* (2006.01)
*C07D 239/47* (2006.01)
*A61K 31/16* (2006.01)
*A61K 31/506* (2006.01)
*A61K 45/06* (2006.01)

(52) U.S. Cl.
CPC ............. *C07D 239/47* (2013.01); *A61K 31/16* (2013.01); *A61K 31/506* (2013.01); *A61K 45/06* (2013.01); *C07D 239/48* (2013.01)

(58) Field of Classification Search
CPC ... C07D 239/48; C07D 239/47; A61K 31/505
USPC ............ 514/272, 275; 544/323, 321; 435/375
See application file for complete search history.

(56) References Cited

U.S. PATENT DOCUMENTS

| | | |
|---|---|---|
| 4,879,303 A | 11/1989 | Davison et al. |
| 5,958,935 A | 9/1999 | Davis et al. |
| 6,093,716 A | 7/2000 | Davis et al. |
| 6,114,333 A | 9/2000 | Davis et al. |
| 6,127,376 A | 10/2000 | Davey et al. |
| 6,160,010 A | 12/2000 | Uckun et al. |
| 6,262,088 B1 | 7/2001 | Phillips |
| 6,469,168 B1 | 10/2002 | Ratzne Simonek et al. |
| 6,579,983 B1 | 6/2003 | Batchelor et al. |
| 6,593,326 B1 | 7/2003 | Bradbury et al. |
| 6,838,464 B2 | 1/2005 | Pease et al. |
| 6,939,874 B2 | 9/2005 | Harmange et al. |
| 7,060,827 B2 | 6/2006 | Singh et al. |
| 7,122,542 B2 | 10/2006 | Singh et al. |
| 7,125,879 B2 | 10/2006 | Guillemont et al. |
| 7,176,212 B2 | 2/2007 | Breault et al. |
| 7,202,033 B2 | 4/2007 | Prescott et al. |
| 7,241,769 B2 | 7/2007 | Stadtmueller et al. |
| 7,282,504 B2 | 10/2007 | Armistead et al. |
| 7,329,671 B2 | 2/2008 | Singh et al. |
| 7,329,672 B2 | 2/2008 | Singh et al. |
| 7,332,484 B2 | 2/2008 | Singh et al. |
| 7,435,814 B2 | 10/2008 | Singh et al. |
| 7,452,879 B2 | 11/2008 | Singh et al. |
| 7,485,724 B2 | 2/2009 | Singh et al. |
| 7,491,732 B2 | 2/2009 | Li et al. |
| 7,498,435 B2 | 3/2009 | Singh et al. |
| 7,504,396 B2 | 3/2009 | Nunes et al. |
| 7,514,444 B2 | 4/2009 | Honigberg et al. |
| 7,514,445 B2 | 4/2009 | Freyne et al. |
| 7,514,446 B2 | 4/2009 | Davis-Ward et al. |
| 7,517,886 B2 | 4/2009 | Singh et al. |
| 7,528,143 B2 | 5/2009 | Noronha et al. |
| 7,531,548 B2 | 5/2009 | Guillemont et al. |
| 7,550,460 B2 | 6/2009 | Singh et al. |
| 7,557,210 B2 | 7/2009 | Singh et al. |
| 7,582,648 B2 | 9/2009 | Singh et al. |
| 7,589,200 B2 | 9/2009 | Singh et al. |
| 7,642,351 B2 | 1/2010 | Singh et al. |
| 7,655,797 B2 | 2/2010 | Singh et al. |
| 7,718,662 B1 | 5/2010 | Chen et al. |
| 7,741,330 B1 | 6/2010 | Chen et al. |
| 7,803,939 B2 | 9/2010 | Singh et al. |
| 7,812,029 B1 | 10/2010 | Singh et al. |
| 7,820,819 B2 | 10/2010 | Singh et al. |
| 7,825,116 B2 | 11/2010 | Singh et al. |
| 7,858,633 B2 | 12/2010 | Li et al. |
| 7,884,111 B2 | 2/2011 | Argade et al. |

(Continued)

FOREIGN PATENT DOCUMENTS

| | | |
|---|---|---|
| CN | 102558149 A | 7/2012 |
| CN | 103159742 A | 6/2013 |

(Continued)

OTHER PUBLICATIONS

International Search Report of PCT/US11/58610 dated Mar. 27, 2012.
International Search Report of PCT/US11/58616 dated Mar. 27, 2012.
International Search Report of PCT/US11/59726 dated Mar. 20, 2012.
Written Opinion of PCT/US11/58610 dated Mar. 27, 2012.
Written Opinion of PCT/US11/58616 dated Mar. 27, 2012.
Written Opinion of PCT/US11/59726 dated Mar. 20, 2012.
U.S. Appl. No. 12/426,495, filed Apr. 20, 2009, Singh et al.

(Continued)

*Primary Examiner* — James O Wilson
*Assistant Examiner* — Ebenezer O Sackey
(74) *Attorney, Agent, or Firm* — Choate, Hall & Stewart LLP; Kristen C. Buteau

(57) ABSTRACT

The present invention provides compounds, pharmaceutically acceptable compositions thereof, and methods of using the same.

17 Claims, 4 Drawing Sheets

(56) References Cited

U.S. PATENT DOCUMENTS

| | | |
|---|---|---|
| 7,906,644 B2 | 3/2011 | Singh et al. |
| 8,088,781 B2 | 1/2012 | Honigberg et al. |
| 8,148,525 B2 | 4/2012 | Singh et al. |
| 8,158,621 B2 | 4/2012 | Singh et al. |
| 8,188,276 B2 | 5/2012 | Singh et al. |
| 8,334,296 B2 | 12/2012 | Singh et al. |
| 8,338,439 B2 | 12/2012 | Singh et al. |
| 8,450,335 B2 | 5/2013 | Singh et al. |
| 8,501,751 B2 | 8/2013 | Honigberg et al. |
| 8,557,806 B2 | 10/2013 | Singh et al. |
| 8,563,568 B2 | 10/2013 | Witowski et al. |
| 8,609,679 B2 | 12/2013 | Singh et al. |
| 8,710,222 B2 | 4/2014 | Singh et al. |
| 8,735,404 B2 | 5/2014 | Honigberg et al. |
| 8,748,438 B2 | 6/2014 | Honigberg et al. |
| 8,748,597 B2 | 6/2014 | Singh et al. |
| 8,796,255 B2 | 8/2014 | Lee et al. |
| 8,822,685 B2 | 9/2014 | Singh et al. |
| 8,835,430 B2 | 9/2014 | Singh et al. |
| 8,853,397 B2 | 10/2014 | Singh et al. |
| 8,883,435 B2 | 11/2014 | Honigberg et al. |
| 8,883,803 B2 | 11/2014 | Honigberg et al. |
| 8,975,249 B2 | 3/2015 | Lee et al. |
| 2004/0002395 A1 | 1/2004 | Poynor |
| 2004/0019067 A1 | 1/2004 | Armistead et al. |
| 2004/0023957 A1 | 2/2004 | Wang et al. |
| 2004/0077661 A1 | 4/2004 | Arbiser |
| 2005/0004125 A1 | 1/2005 | Freyne et al. |
| 2005/0014753 A1 | 1/2005 | Ding et al. |
| 2005/0085637 A1 | 4/2005 | Cheung et al. |
| 2005/0209221 A1 | 9/2005 | Nunes et al. |
| 2005/0272083 A1 | 12/2005 | Seshagiri |
| 2006/0030018 A1 | 2/2006 | Zuccola et al. |
| 2006/0079543 A1 | 4/2006 | Sum et al. |
| 2006/0084644 A1 | 4/2006 | Pal et al. |
| 2006/0084645 A1 | 4/2006 | Pal et al. |
| 2006/0100227 A1 | 5/2006 | Baenteli et al. |
| 2006/0148800 A1 | 7/2006 | Stadtmueller et al. |
| 2006/0160803 A1 | 7/2006 | Adams et al. |
| 2006/0247241 A1 | 11/2006 | Garcia-Echeverria et al. |
| 2006/0247262 A1 | 11/2006 | Baenteli et al. |
| 2006/0270694 A1 | 11/2006 | Wong |
| 2006/0293311 A1 | 12/2006 | Li et al. |
| 2007/0010668 A1 | 1/2007 | Davis-Ward et al. |
| 2007/0032493 A1 | 2/2007 | Foley et al. |
| 2007/0066658 A1 | 3/2007 | Chappell |
| 2007/0203161 A1 | 8/2007 | Argade et al. |
| 2007/0203162 A1 | 8/2007 | Li et al. |
| 2007/0259904 A1 | 11/2007 | Noronha et al. |
| 2008/0009484 A1 | 1/2008 | Argade et al. |
| 2008/0009494 A1 | 1/2008 | Li et al. |
| 2008/0021020 A1 | 1/2008 | Argade et al. |
| 2008/0027045 A1 | 1/2008 | Argade et al. |
| 2008/0039622 A1 | 2/2008 | Singh et al. |
| 2008/0058358 A1 | 3/2008 | Luecking et al. |
| 2008/0076921 A1 | 3/2008 | Honigberg et al. |
| 2008/0132504 A1 | 6/2008 | Garcia-Echeverria et al. |
| 2008/0139582 A1 | 6/2008 | Honigberg et al. |
| 2008/0167330 A1 | 7/2008 | Luecking et al. |
| 2008/0176866 A1 | 7/2008 | Jautelat et al. |
| 2008/0182852 A1 | 7/2008 | Johnson et al. |
| 2008/0194603 A1 | 8/2008 | Li et al. |
| 2008/0194605 A1 | 8/2008 | Heinrich et al. |
| 2008/0207613 A1 | 8/2008 | Styles et al. |
| 2008/0214501 A1 | 9/2008 | Pan et al. |
| 2008/0260754 A1 | 10/2008 | Li et al. |
| 2008/0279867 A1 | 11/2008 | Atuegbu et al. |
| 2008/0300268 A1 | 12/2008 | Singh et al. |
| 2008/0312438 A1 | 12/2008 | Singh et al. |
| 2009/0131436 A1 | 5/2009 | Imbach et al. |
| 2009/0137588 A1 | 5/2009 | Singh et al. |
| 2009/0156622 A1 | 6/2009 | Singh et al. |
| 2009/0171086 A1 | 7/2009 | Singh et al. |
| 2009/0181987 A1 | 7/2009 | Honigberg et al. |
| 2009/0215803 A1 | 8/2009 | Rice et al. |
| 2009/0286778 A1 | 11/2009 | Combs et al. |
| 2009/0298830 A1 | 12/2009 | Mann et al. |
| 2009/0318407 A1 | 12/2009 | Bauer et al. |
| 2010/0004270 A1 | 1/2010 | Honigberg et al. |
| 2010/0016296 A1 | 1/2010 | Singh et al. |
| 2010/0022561 A1 | 1/2010 | Honigberg et al. |
| 2010/0029610 A1 | 2/2010 | Singh et al. |
| 2010/0041677 A1 | 2/2010 | Honigberg et al. |
| 2010/0081679 A1 | 4/2010 | Greul et al. |
| 2010/0088912 A1 | 4/2010 | Higgs et al. |
| 2010/0173285 A1 | 7/2010 | Varmus et al. |
| 2010/0197918 A1 | 8/2010 | Singh et al. |
| 2010/0249092 A1 | 9/2010 | Singh et al. |
| 2010/0254905 A1 | 10/2010 | Honigberg et al. |
| 2011/0039868 A1 | 2/2011 | Honigberg et al. |
| 2011/0105472 A1 | 5/2011 | Greul et al. |
| 2011/0144330 A1 | 6/2011 | Singh et al. |
| 2011/0207736 A1 | 8/2011 | Gray et al. |
| 2011/0224235 A1 | 9/2011 | Honigberg et al. |
| 2011/0245156 A1 | 10/2011 | Sielecki-Dzurdz |
| 2011/0245284 A1 | 10/2011 | Greul et al. |
| 2011/0281322 A1 | 11/2011 | Honigberg et al. |
| 2011/0281850 A1 | 11/2011 | Flynn et al. |
| 2012/0040968 A1 | 2/2012 | Shimada et al. |
| 2012/0065201 A1 | 3/2012 | Honigberg et al. |
| 2012/0071497 A1 | 3/2012 | Buggy et al. |
| 2012/0077832 A1 | 3/2012 | Witowski et al. |
| 2012/0083006 A1 | 4/2012 | Ramsden et al. |
| 2012/0087915 A1 | 4/2012 | Buggy et al. |
| 2012/0088912 A1 | 4/2012 | Honigberg et al. |
| 2012/0094999 A1 | 4/2012 | Gray et al. |
| 2012/0101113 A1 | 4/2012 | Honigberg et al. |
| 2012/0101114 A1 | 4/2012 | Honigberg et al. |
| 2012/0149687 A1 | 6/2012 | Lee et al. |
| 2012/0149722 A1 | 6/2012 | Lee et al. |
| 2012/0157426 A1 | 6/2012 | Lee et al. |
| 2012/0165328 A1 | 6/2012 | Honigberg et al. |
| 2012/0165332 A1 | 6/2012 | Major et al. |
| 2012/0184013 A1 | 7/2012 | Honigberg et al. |
| 2012/0184567 A1 | 7/2012 | Honigberg et al. |
| 2012/0202264 A1 | 8/2012 | Honigberg et al. |
| 2012/0270237 A9 | 10/2012 | Ramsden et al. |
| 2012/0296089 A1 | 11/2012 | Honigberg et al. |
| 2012/0316135 A1 | 12/2012 | Dalgarno et al. |
| 2012/0329130 A1 | 12/2012 | Honigberg et al. |
| 2013/0035334 A1 | 2/2013 | Honigberg et al. |
| 2013/0065879 A1 | 3/2013 | Singh et al. |
| 2013/0065899 A1 | 3/2013 | Singh et al. |
| 2013/0072469 A1 | 3/2013 | Singh et al. |
| 2013/0137708 A1 | 5/2013 | Garske et al. |
| 2013/0165462 A1 | 6/2013 | Singh et al. |
| 2014/0057929 A1 | 2/2014 | Witowski et al. |
| 2014/0134265 A1 | 5/2014 | Buggy et al. |
| 2014/0142123 A1 | 5/2014 | Honigberg et al. |
| 2014/0163027 A1 | 6/2014 | Verner et al. |
| 2014/0163046 A1 | 6/2014 | Honigberg et al. |
| 2014/0187564 A1 | 7/2014 | Honigberg et al. |
| 2014/0187565 A1 | 7/2014 | Honigberg et al. |
| 2014/0213574 A1 | 7/2014 | Singh et al. |
| 2014/0303154 A1 | 10/2014 | Singh et al. |
| 2014/0303191 A1 | 10/2014 | Buggy et al. |
| 2014/0330007 A1 | 11/2014 | Singh et al. |
| 2014/0371241 A1 | 12/2014 | Buggy et al. |
| 2015/0005297 A1 | 1/2015 | Singh et al. |
| 2015/0025055 A1 | 1/2015 | Lee et al. |
| 2015/0038518 A1 | 2/2015 | Balasubramanian |
| 2015/0126504 A1 | 5/2015 | Singh et al. |
| 2015/0158823 A1 | 6/2015 | Singh et al. |

FOREIGN PATENT DOCUMENTS

| | | |
|---|---|---|
| EP | 1054004 A1 | 11/2000 |
| JP | 07041461 | 2/1995 |
| WO | WO-96/28427 A1 | 9/1996 |
| WO | WO-97/19065 A1 | 5/1997 |
| WO | WO-00/27825 A1 | 5/2000 |
| WO | WO-00/46203 A2 | 8/2000 |
| WO | WO-00/78731 A1 | 12/2000 |
| WO | WO-01/47897 A1 | 7/2001 |

(56) References Cited

FOREIGN PATENT DOCUMENTS

| WO | WO-01/60816 A1 | 8/2001 |
| WO | WO-01/64654 A1 | 9/2001 |
| WO | WO-01/64655 A1 | 9/2001 |
| WO | WO-01/85699 A2 | 11/2001 |
| WO | WO-02/083653 A1 | 10/2002 |
| WO | WO-03/016306 A1 | 2/2003 |
| WO | WO-03/030909 A1 | 4/2003 |
| WO | WO-03/063794 A2 | 8/2003 |
| WO | WO-03/066601 A1 | 8/2003 |
| WO | WO-2004/014382 A1 | 2/2004 |
| WO | WO-2004/031232 A1 | 4/2004 |
| WO | WO-2004/056786 A2 | 7/2004 |
| WO | WO-2004/069812 A1 | 8/2004 |
| WO | WO-2004/074244 A2 | 9/2004 |
| WO | WO-2004/080980 A1 | 9/2004 |
| WO | WO-2004096224 A2 | 11/2004 |
| WO | WO-2005/013996 A1 | 2/2005 |
| WO | WO-2005/016893 A2 | 2/2005 |
| WO | WO-2005/016894 A1 | 2/2005 |
| WO | WO-2005/026130 A1 | 3/2005 |
| WO | WO-2005/026158 A1 | 3/2005 |
| WO | WO-2005/063722 A1 | 7/2005 |
| WO | WO-2005/070890 A2 | 8/2005 |
| WO | WO-2006/021544 A1 | 3/2006 |
| WO | WO-2006/045066 A2 | 4/2006 |
| WO | WO-2006/053109 A1 | 5/2006 |
| WO | WO-2006/055561 A1 | 5/2006 |
| WO | WO-2006/068770 A1 | 6/2006 |
| WO | WO-2006/074057 A2 | 7/2006 |
| WO | WO-2006/078846 A1 | 7/2006 |
| WO | WO-2006/101977 A2 | 9/2006 |
| WO | WO-2006/108487 A1 | 10/2006 |
| WO | WO-2006/124874 A2 | 11/2006 |
| WO | WO-2006/128129 A2 | 11/2006 |
| WO | WO-2006/129100 A1 | 12/2006 |
| WO | WO-2006/133426 A2 | 12/2006 |
| WO | WO-2007/027238 A2 | 3/2007 |
| WO | WO-2007/048064 A2 | 4/2007 |
| WO | WO-2007/053452 A1 | 5/2007 |
| WO | WO-2007/056151 A2 | 5/2007 |
| WO | WO-2007/085833 A2 | 8/2007 |
| WO | WO-2007/089768 A2 | 8/2007 |
| WO | WO-2007/113254 A1 | 10/2007 |
| WO | WO-2007/113256 A1 | 10/2007 |
| WO | WO-2007/120339 A1 | 10/2007 |
| WO | WO-2007/120980 A2 | 10/2007 |
| WO | WO-2007/125351 A1 | 11/2007 |
| WO | WO-2008/005538 A2 | 1/2008 |
| WO | WO-2008/009458 A1 | 1/2008 |
| WO | WO-2008/025556 A1 | 3/2008 |
| WO | WO-2008/049123 A2 | 4/2008 |
| WO | WO-2008/064274 A1 | 5/2008 |
| WO | WO-2008/073687 A2 | 6/2008 |
| WO | WO-2008/074515 A1 | 6/2008 |
| WO | WO-2008/079719 A1 | 7/2008 |
| WO | WO-2008/079907 A1 | 7/2008 |
| WO | WO-2008/080964 A1 | 7/2008 |
| WO | WO-2008/080965 A2 | 7/2008 |
| WO | WO-2008/088303 A1 | 7/2008 |
| WO | WO-2008/092199 A1 | 8/2008 |
| WO | WO-2008/107096 A1 | 9/2008 |
| WO | WO-2008/115738 A1 | 9/2008 |
| WO | WO-2008/115742 A1 | 9/2008 |
| WO | WO-2008/118822 A1 | 10/2008 |
| WO | WO-2008/118823 A2 | 10/2008 |
| WO | WO-2009/012421 A1 | 1/2009 |
| WO | WO-2009/017838 A2 | 2/2009 |
| WO | WO-2009/029682 A1 | 3/2009 |
| WO | WO-2009/032668 A2 | 3/2009 |
| WO | WO-2009/032694 A1 | 3/2009 |
| WO | WO-2009/032703 A1 | 3/2009 |
| WO | WO-2009/080638 A2 | 7/2009 |
| WO | WO-2009/105675 A1 | 8/2009 |
| WO | WO-2009/112490 A1 | 9/2009 |
| WO | WO-2009/115267 A2 | 9/2009 |
| WO | WO-2009/127642 A2 | 10/2009 |
| WO | WO-2009/143389 A1 | 11/2009 |
| WO | WO-2009/158571 A1 | 12/2009 |
| WO | WO-2010/025833 A1 | 3/2010 |
| WO | WO-2010/081679 A2 | 7/2010 |
| WO | WO-2010/129053 A2 | 11/2010 |
| WO | WO-2011/079231 A1 | 6/2011 |
| WO | WO-2011/090760 A1 | 7/2011 |
| WO | WO-2011/140338 A1 | 11/2011 |
| WO | WO-2011/153514 A2 | 12/2011 |
| WO | WO-2012/021444 A1 | 2/2012 |
| WO | WO-2012/061299 A1 | 5/2012 |
| WO | WO-2012/061303 A1 | 5/2012 |
| WO | WO-2012/061415 A1 | 5/2012 |
| WO | WO-2012/064706 A1 | 5/2012 |
| WO | WO-2012/158843 A2 | 11/2012 |

OTHER PUBLICATIONS

U.S. Appl. No. 12/648,693, filed Dec. 29, 2009, Singh et al.
U.S. Appl. No. 13/286,061, filed Oct. 31, 2011, Lee et al.
U.S. Appl. No. 13/286,062, filed Oct. 31, 2011, Lee et al.
U.S. Appl. No. 13/291,706, filed Nov. 8, 2011, Lee et al.
Aliagas-Martin, I. et al., A class of 2,4-bisanilinopyrimidine Aurora A inhibitors with unusually high selectivity against Aurora B, J. Med. Chem. 52:3300-3307 (2009).
Andrulis, I. et al., Neu/ErbB-2 amplification identifies a poor-prognosis group of women with node-negative breast cancer, J Clin Oncol 16:1340-9 (1998).
Bamborough, P. et al., N-4-Pyrimidinyl-1H-indazol-4-amine inhibitors of Lck: Indazoles as phenol isosteres with improved pharmacokinetics, Bioorg. & Med. Chem. Lett. 17:4363-4368 (2007).
Carter, T. et al, Inhibition of drug-resistant mutants of ABL, KIT, and EGF receptor kinases, Proc. Natl. Acad. Sci. USA 102(31):11011-11016 (2005).
Cohen, M. et al., Structural bioinformatics-based design of selective, irreversible inhibitors, Science 308:1318-1321 (2005).
Curto, M. et al., Contact-dependent inhibition of EGFR signaling by Nf2/Merlin, J Cell Biol 177:893-903 (2007).
Ding, K. et al., Design, Synthesis and Biological Evaluation of Novel Conformationally Constrained Inhibitors Targeting Epidermal Growth Factor Receptor T790M mutant, J. Med. Chem. Feb. 16, 2012, DOI: 10.1021/jm201591k.
Fallon, K. et al., Constitutive activation of the neuregulin-1/erbB signaling pathway promotes the proliferation of a human peripheral neuroepithelioma cell line, J Neuro Oncol 66:273-84 (2004).
Frank, D., STAT signaling in the pathogenesis and treatment of cancer, Mol. Med. 5 :432-456 (1999).
Fry, D. et al., Specific, irreversible inactivation of the epidermal growth factor receptor and erbB2, by a new class of tyrosine kinase inhibitor, Proc. Natl. Acad. Sci. USA 95:12022-12027 (1998).
Ghoneim, K., Synthesis and evaluation of some 2-, 4-, di-substituted-6-methylpyrimidine derivatives for antimicrobial activity, J. Indian Chem. Soc. 63(10):914-917 (1986).
Ghosh, D., 2-4-bis (arylamino)-5-methylpyrimidines as antimicrobial agents, J. Med. Chem. 10(5):974 (1967).
Ghosh, D., 2-4-bis (arylamino)-6-methylpyrimidines as antimicrobial agents, J. Indian Chem. Soc. 58(5):512-573 (1981).
Gonzales, A. et al, Antitumor activity and pharmacokinetic properties of PF-00299804, a second-generation, irreversible pan-erbB receptor tyrosine kinase inhibitor, Mol. Cancer Ther. 7(7):1880-1889 (2008).
Hur, W. et al., Clinical stage EGFR inhibitors irreversibly alkylate Bmx kinase, Bioorg. Med. Chem. Lett. 18:5916-5919 (2008).
International Search Report of PCT/US09/48784 (Publication No. WO 2009/158571) dated Nov. 16, 2009.
International Search Report of PCT/US10/31714 (Publication No. WO 2010/123870) dated Aug. 13, 2010.
International Search Report of PCT/US10/62432 (Publication No. WO 2011/090760) dated May 26, 2011.
Kirken, R., Targeting Jak3 for immune suppression and allograft acceptance, Transplant. Proc. 33 :3268-3270 (2001).

(56) References Cited

OTHER PUBLICATIONS

Kwak, E. et al., Irreversible inhibitors of the EGF receptor may circumvent acquired resistance to gefitinib, Proc. Natl. Acad. Sci. USA 102:7665-7670 (2005).

Lajeunesse, D. et al., A systematic screen for dominant second-site modifiers of Merlin/NF2 phenotypes reveals an interaction with blistered/DSRF and scribbler, Genetics 158:667-79 (2001).

Li, D. et al., BIBW2992, an irreversible EGFR/HER2 inhibitor highly effective in preclinical lung cancer models, Oncogene 27:4702-4711 (2008).

Lin, N. and Winer, E., New targets for therapy in breast cancer: Small molecule tyrosine kinase inhibitors, Breast Cancer Res 6:204-210 (2004).

Malaviya, R. et al., Targeting Janus Kinase 3 in Mast Cells Prevents Immediate Hypersensitivity Reactions and Anaphylaxis, J. Biol. Chem. 274 :27028-27038 (1999).

McClatchey, A. and Giovannini, M., Membrane organization and tumorigenesis—the NF2 tumor suppressor, Merlin, Genes Dev 19:2265-77 (2005).

Minkovsky, N. and Berezov, A., BIBW-2992, a dual receptor tyrosine kinase inhibitor for the treatment of solid tumors, Curr Opin Invest Drugs 9:1336-1346 (2008).

Pelton, P. et al., Ruffling membrane, stress fiber, cell spreading and proliferation abnormalities in human Schwann cells, Oncogene 17:2195-2209 (1998).

PubChem CID 44594695. Feb. 1, 2010. [Retrieved from the Internet May 15, 2011: http://pubchem.ncbi.nlm.nih.gov/summary.cgi?cid=44594695&loc=ec_rcs].

Readinger, J. et al., Selective Targeting of ITK Blocks Multiple Steps of HIV Replication, Proc. Natl. Acad. Sci. USA 105: 6684-6689 (2008).

Seidel, H. et al., Pharmaceutical intervention in the JAK/STAT signaling pathway, Oncogene 19: 2645-2656 (2000).

Sequist, L., Second-Generation Epidermal Growth Factor Receptor Tyrosine Kinase Inhibitors in Non-Small Cell Lung Cancer, The Oncologist 12(3):325-330 (2007).

Singh, J. et al, Structure-based design of a potent, selective, and irreversible inhibitor of the catalytic domain of the erbB receptor subfamily of protein tyrosine kinases, J. Med. Chem. 40:1130-1135 (1997).

Stonecypher, M. et al., Activation of the neuregulin-1/ErbB signaling pathway promotes the proliferation of neoplastic Schwann cells in human malignant peripheral nerve sheath tumors, Oncogene 24:5589-5605 (2005).

Sudbeck, E. et al., Structure-based Design of Specific Inhibitors of Janus Kinase 3 as Apoptosis-inducing Antileukemic Agents, Clin. Cancer Res. 5: 1569-1582 (1999).

Trieu, V. et al., A specific inhibitor of janus kinase-3 increases survival in a transgenic mouse model of amyotrophic lateral sclerosis, Biochem. Biophys. Res. Commun. 267 :22-25 (2000).

Wong, K. et al, A phase I study with neratinib (HKI-272), an irreversible pan Erb B receptor tyrosine kinase inhibitor, in patients with solid tumors, Clin. Cancer Res. 15(7):2552-2558 (2009).

Written Opinion of PCT/US09/48784 (Publication No. WO 2009/158571) mailed Nov. 16, 2009.

Written Opinion of PCT/US10/31714 (Publication No. WO 2010/123870) dated Aug. 13, 2010.

Written Opinion of PCT/US10/62432 (Publication No. WO 2011/090760) dated May 26, 2011.

Zhang, J. et al., Targeting Cancer with Small Molecule Kinase Inhibitors, Nature Rev. Cancer 9:28-39 (2009).

Zhang, Y. et al., Antitumor Activity of Epidermal Growth Factor Receptor-Related Protein Is Mediated by Inactivation of ErbB Receptors and Nuclear Factor-kB in Pancreatic Cancer, Cancer Res 66:1025-1032 (2006).

Zhou, W. et al. Novel mutant-selective EGFR kinase inhibitors against EGFR T790M, Nature. Dec. 24, 2009; 462(7276): 1070-1074.

U.S. Appl. No. 13/518,833, filed Jun. 22, 2012, Gray et al.
U.S. Appl. No. 13/667,396, filed Nov. 2, 2012, Singh et al.
U.S. Appl. No. 13/671,112, filed Nov. 7, 2012, Singh et al.
U.S. Appl. No. 13/670,937, filed Nov. 7, 2012, Singh et al.
U.S. Appl. No. 13/671,129, filed Nov. 7, 2012, Singh et al.
U.S. Appl. No. 14/058,847, Oct. 21, 2013, Celgene Avilomics Research, Inc.

International Search Report for PCT/US11/46926, Publication No. WO 2012/021444 (mailed Dec. 22, 2011).

Written Opinion for PCT/US11/46926, Publication No. WO 2012/021444 (mailed Dec. 22, 2011).

U.S. Appl. No. 14/448,578, filed Jul. 31, 2014, Lee et al.

Calvo et al., Administration of CI-1033, an Irreversible Pan-erbB Tyrosine Kinase Inhibitor, Is Feasible on a 7-Day Off Schedule: A Phase I Pharmacokinetic and Food Effect Study, Clin. Can. Res., 10:7112-7120(2004).

Extended European Search Report for EP11838624.2, 5 pages (Jun. 6, 2014).

Extended European Search Report for EP11838628.3, 7 pages (Jun. 20, 2014).

Extended European Search Report for EP11839800.7, 8 pages (Jun. 24, 2014).

Fabian et al., A small molecule-kinase interaction map for clinical kinase inhibitors, Nat. Biotech., 23(3):329(2005).

Supplementary European Search Report for EP10844293.0, 8 pages (Jun. 27, 2013).

Extended European Search Report for EP11816874.9, 5 pages (Dec. 12, 2014).

U.S. Appl. No. 14/636,905, filed Mar. 3, 2015, Lee et al.

Kumar, A., et al, Structure and Clinical Relevance of the Epidermal Growth Factor Receptor in Human Cancer, Journal of Clinical Oncology 26(10):1742-1751 (2008).

| COMPOUND-ID | H1975 (EGFR L858R/T790M) EC₅₀ (nM) | | A431 (EGFR WT) EC₅₀ (nM) | |
| --- | --- | --- | --- | --- |
| | pEGFR | pS6 Ribosomal | pEGFR | pS6 Ribosomal |
| I-3 | 10-100 | 10-100 | >1000 | >1000 |
| I-7 | 10-100 | 10-100 | >1000 | >1000 |

FIGURE 2

HETEROARYL COMPOUNDS AND USES THEREOF

CROSS-REFERENCE TO RELATED APPLICATIONS

The present application claims priority to U.S. Provisional Patent Applications 61/534,306, filed Sep. 13, 2011, 61/412,324, filed Nov. 10, 2010, 61/411,834. filed Nov. 9, 2010 and 61/409,074, filed Nov. 1, 2010, the entire contents of each of which are herein incorporated by reference.

TECHNICAL FIELD OF THE INVENTION

The present invention relates to compounds useful as mutant-selective epidermal growth factor receptor (EGFR) kinase inhibitors. The invention also provides pharmaceutically acceptable compositions comprising compounds of the present invention and methods of using said compositions in the treatment of various disorders.

BACKGROUND OF THE INVENTION

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

There is strong precedent for involvement of the EGFR in human cancer because over 60% of all solid tumors overexpress at least one of these proteins or their ligands. Overexpression of EGFR is commonly found in breast, lung, head and neck, bladder tumors.

Activating mutations in the tyrosine kinase domain of EGFR have been identified in patients with non-small cell lung cancer (Lin, N. U.; Winer, E. P., Breast Cancer Res 6: 204-210, 2004). The reversible inhibitors Tarceva (erlotinib) and Iressa (gefitinib) currently are first-line therapy for non-small cell lung cancer patients with activating mutations. The most common activating mutations are L858R and delE746-A750.

Additionally, in the majority of patients that relapse, acquired drug resistance, such as by mutation of gatekeeper residue T790M, has been detected in at least half of such clinically resistant patients. Moreover, T790M may also be pre-existing, there may be an independent, oncogenic role for the T790M mutation. For example, there are patients with the L858R/T790M mutation who never received gefitinib treatment. In addition, germline EGFR T790M mutations are linked with certain familial lung cancers.

Current drugs in development, including second generation covalent inhibitors, such as BIBW2992, HKI-272 and PF-0299804, are effective against the T790M resistance mutation but exhibit dose-limiting toxicities due to concurrent inhibition of WT EGFR. Accordingly, there remains a need to find mutant-selective EGFR kinase inhibitors useful as therapeutic agents.

SUMMARY OF THE INVENTION

It has now been found that compounds of this invention, and pharmaceutically acceptable compositions thereof, are effective as mutant-selective EGFR kinase inhibitors. Such compounds have general formula I:

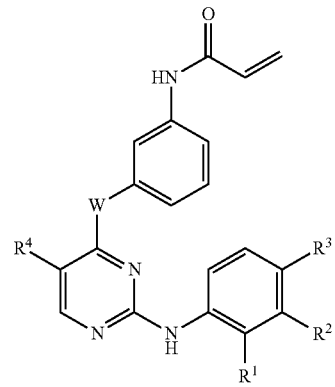

I or a pharmaceutically acceptable salt thereof, wherein each of W, $R^1$, $R^2$, $R^3$, and $R^4$ is as defined and described herein.

Compounds of the present invention, and pharmaceutically acceptable compositions thereof, are useful for treating cancers associated with one or more EGFR mutations. Such diseases, disorders, or conditions include those described herein.

Compounds provided by this invention are also useful for the study of kinases in biological and pathological phenomena; the study of intracellular signal transduction pathways mediated by such kinases; and the comparative evaluation of new kinase inhibitors.

BRIEF DESCRIPTION OF THE DRAWINGS

FIG. 2 depicts the selective dose-response inhibition of pS6 ribosomal protein in mutant EGFR cells as compared to wild type EGFR with test compounds I-3 and I-7.

DETAILED DESCRIPTION OF CERTAIN EMBODIMENTS

Figure 1:
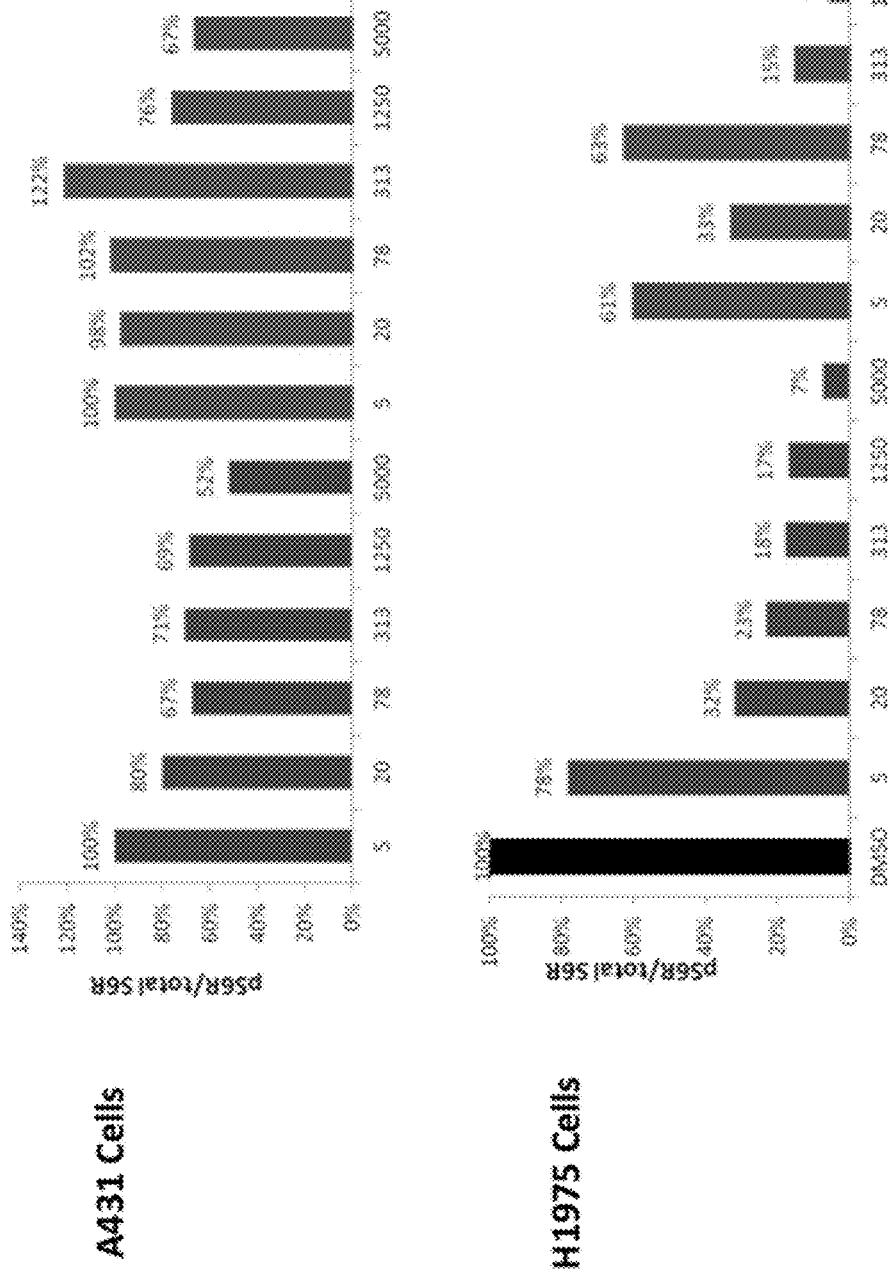
FIG. 1 depicts dose-response inhibition of pS6 ribosomal protein with test compounds I-3 and I-7.

1. General Description of Compounds of the Invention

In certain embodiments, the present invention provides a compound of formula I:

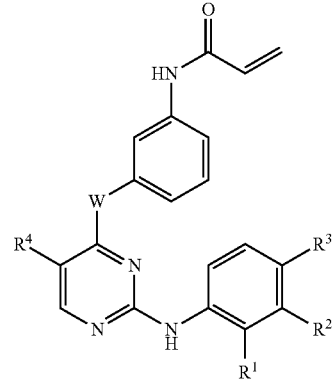

I or a pharmaceutically acceptable salt thereof, wherein:

W is —O— or —NH—;

$R^1$ is —OR;

each R is independently $C_{1-4}$ alkyl or $C_{1-4}$ fluoroalkyl;

each of $R^2$ and $R^3$ is independently hydrogen, —OH, or —OR; and $R^4$ is —$CF_3$, Cl, or Br.

As defined generally above, $R^1$ is —OR wherein R is $C_{1-4}$ alkyl or $C_{1-4}$ fluoroalkyl. In some embodiments, R is $C_{1-4}$ alkyl. In certain embodiments, R is $C_{1-4}$ fluoroalkyl. In some embodiments, R is —$CHF_2$ or —$CF_3$.

In some embodiments, the present invention provides a compound of formula I wherein at least one; at least two; at least three; or all of the following characteristics apply:

(a) W is —O—;
(b) $R^1$ is —$OCH_3$;
(c) $R^2$ is hydrogen or —$OCH_3$;
(d) $R^3$ is hydrogen or —$OCH_3$; or
(e) $R^4$ is —$CF_3$ or —Cl.

In some embodiments, the present invention provides a compound of formula I wherein at least one; at least two; at least three; or all of the following characteristics apply:

(a) W is —NH—;
(b) $R^1$ is —$OCH_3$;
(c) $R^2$ is hydrogen or —$OCH_3$;
(d) $R^3$ is hydrogen or —$OCH_3$; or
(e) $R^4$ is —$CF_3$ or —Cl.

In some embodiments, the present invention provides a compound of formula I wherein at least one; at least two; at least three; or all of the following characteristics apply:

(a) W is —O— or —NH—;
(b) $R^1$ is —$OCH_3$;
(c) $R^2$ is hydrogen or —$OCH_3$;
(d) $R^3$ is hydrogen or —$OCH_3$; or
(e) $R^5$ is —$CF_3$ or —Cl.

Exemplary compounds of formula I are set forth in Table 1, below.

TABLE 1

Exemplary Compounds

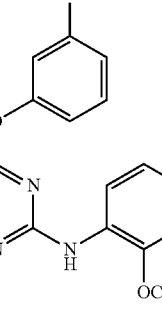

I-1

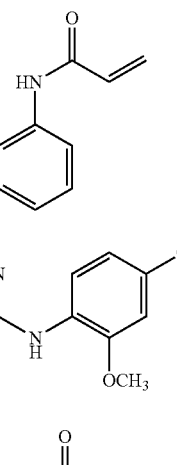

I-2

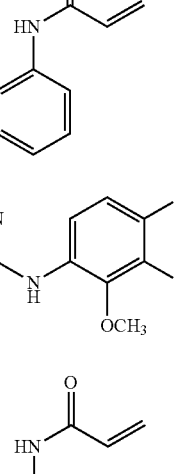

I-3

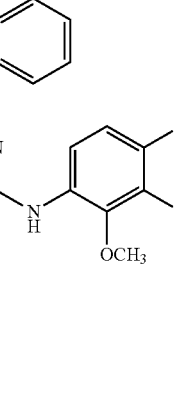

I-4, I-5

TABLE 1-continued
Exemplary Compounds
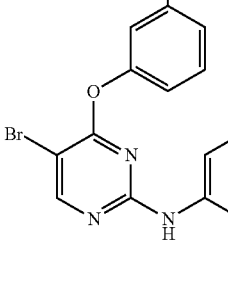 I-6
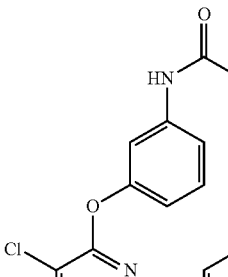 I-7
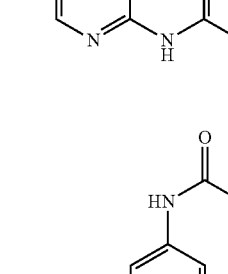 I-8
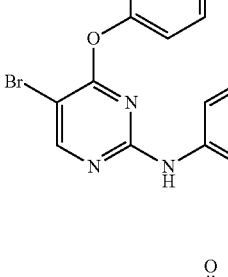 I-9
TABLE 1-continued
Exemplary Compounds
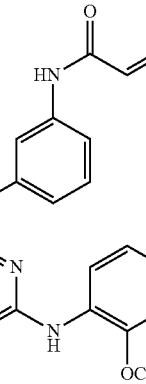 I-10
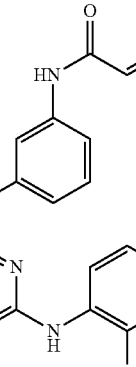 I-11
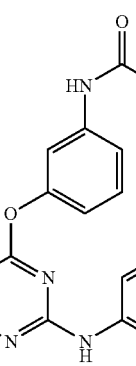 I-12
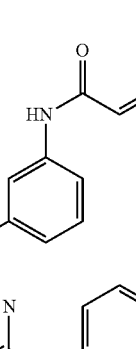 I-13

TABLE 1-continued
Exemplary Compounds
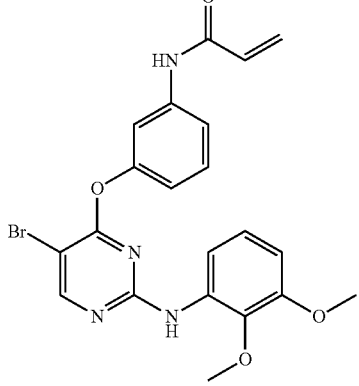
I-14
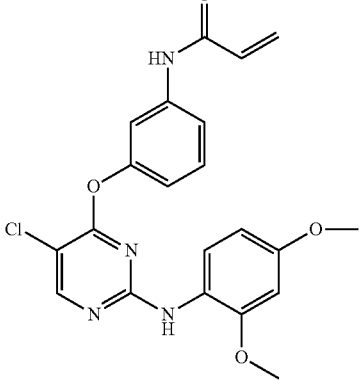
I-15
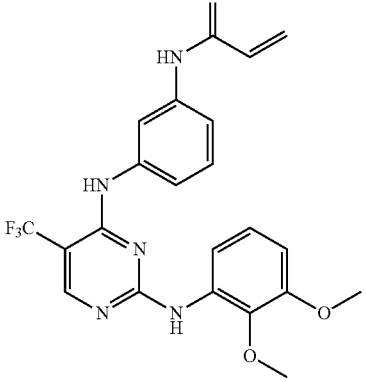
I-16
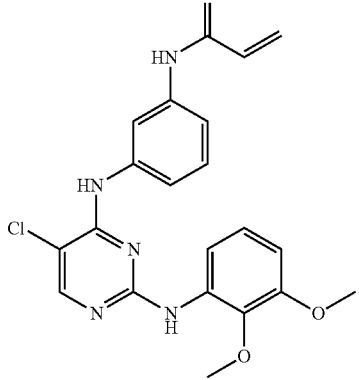
I-17
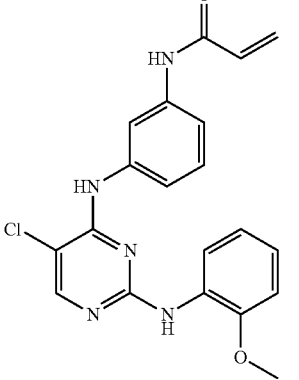
I-18
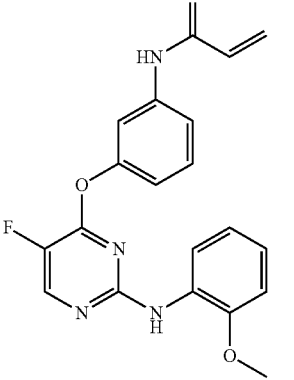
I-19
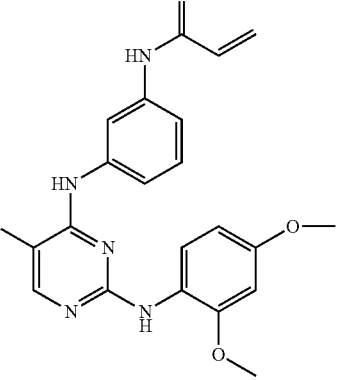
I-20
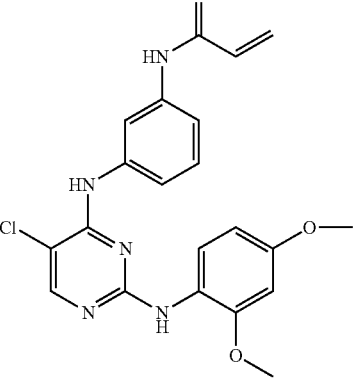
I-21

TABLE 1-continued

Exemplary Compounds

I-22

[Structure: N-(3-((5-bromo-2-((2-methoxyphenyl)amino)pyrimidin-4-yl)amino)phenyl)acrylamide]

I-23

[Structure: N-(3-((2-((2,3-dimethoxyphenyl)amino)-5-(trifluoromethyl)pyrimidin-4-yl)oxy)phenyl)acrylamide]

In certain embodiments, the present invention provides a compound set forth in Table 1, above, or a pharmaceutically acceptable salt thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $n^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

2. Description of Exemplary Embodiments

As described in detail herein, infra, provided compounds are selective inhibitors of at least one mutation of EGFR. It has been surprisingly found that provided compounds are selective inhibitors of at least one mutation of EGFR as compared to wild-type ("WT") EGFR. In certain embodiments, an at least one mutation of EGFR is T790M. In certain embodiments, the at least one mutation of EGFR is a deletion mutation. In some embodiments, the at least one mutation of EGFR is an activating mutation. In certain embodiments, a provided compound selectively inhibits at least one deletion/resistant mutation and at least one activating mutation as compared to WT EGFR. In some embodiments, a provided compound selectively inhibits at least one deletion and/or at least one point mutation, and is sparing as to WT EGFR inhibition.

A mutation of EGFR can be selected from T790M (resistant or oncogenic), L858R (activating), delE746-A750 (activating), G719S (activating), or a combination thereof.

As used herein, the term "selectively inhibits," as used in comparison to inhibition of WT EGFR, means that a provided compound inhibits at least one mutation of EGFR (i.e., at least one deletion mutation, at least one activating mutation, or a combination of at least one deletion mutation and at least one activating mutation) in at least one assay described herein (e.g., biochemical or cellular). In some embodiments, the term "selectively inhibits," as used in comparison to WT EGFR inhibition means that a provided compound is at least 50 times more potent, at least 45 times, at least 40, at least 35, at least 30, at least 25, or at least 20 times more potent as an inhibitor of at least one mutation of EGFR, as defined and described herein, as compared to WT EGFR.

As used herein, the term "sparing as to WT EGFR" means that a selective inhibitor of at least one mutation of EGFR, as defined and described above and herein, inhibits EGFR at the upper limit of detection of at least one assay as described herein (e.g., biochemical or cellular as described in detail in Examples 24-26). In some embodiments, the term "sparing as to WT EGFR" means that a provided compound inhibits WT EGFR with an $IC_{50}$ of at least 10 µM, at least 9 µM, at least 8 µM, at least 7 µM, at least 6 µM, at least 5 µM, at least 3 µM, at least 2 µM, or at least 11 µM.

In certain embodiments, a provided compound selectively inhibits (a) at least one activating mutation; and (b) T790M; and (c) is sparing as to WT. In some embodiments, an at least one activating mutation is a deletion mutation. In some embodiments, an at least one activating mutation is a point mutation. In some embodiments, an activating mutation is L858R. In some embodiments, an activating mutation is G719S. In some embodiments, an activating mutation is delE746-A750.

In some embodiments, the at least one mutation of EGFR is L858R and/or T790M.

Without wishing to be bound by any particular theory, it is believed that administration of a provided compound to a patient having at least one activating mutation may preempt formation of the T790M resistance mutation. Thus, in certain embodiments, the present invention provides a method for inhibiting an activating mutation in a patient comprising administering to the patient a provided compound or composition thereof, as described herein.

One of ordinary skill in the art will appreciate that certain patients have an oncogenic form of the T790M mutation, i.e., the T790M mutation is present prior to administration to the patient any EGFR inhibitor and is therefore oncogenic. Accordingly, in some embodiments, the present invention provides a method for inhibiting oncogenic T790M in a patient comprising administering to the patient a provided compound or composition thereof, as described herein.

Tarceva (erlotinib) and Iressa (gefitinib) are first-line therapies for patients with activating mutations but exhibit dose-limiting toxicities due to concurrent inhibition of WT EGFR. In addition, drugs currently in development, including second generation covalent inhibitors, such as BIBW2992, HKI-272 and PF-0299804, are effective against the T790M resistance mutation but exhibit dose-limiting toxicities due to concurrent inhibition of WT EGFR.

It has been surprisingly found that provided compounds selectively inhibit each of the EGFR activating and deletion mutations. Moreover, provided compounds are sparing for WT EGFR and associated dose-limiting toxicities.

This stands in contrast to other known EGFR inhibitors (e.g., BIBW2992 and HKI-272) which are only somewhat effective against mutants but retain activity against WT EGFR and are therefore limited by toxicities associated with inhibition of WT EGFR. Table 2, below, sets forth $GI_{50}$ values of Tarceva, BIBW2992 and HKI-272 as compared with provided compounds I-1 and I-11 (where compound numbers correspond to compound numbers in Table 1, supra). The data shown in Table 2 correspond to $GI_{50}$ values obtained in the cellular proliferation assay described in detail in Example 26, where A431 cells express WT EGFR, HCC827 express EGFR having the deletion mutation delE746-A750, and H1975 cells express EGFR having a double mutation L858R/T790M.

TABLE 2

Comparative $GI_{50}$ Values (nM)

| Cell Line | Tarceva | BIBW2992 | HKI-272 | I-1 | I-11 |
|---|---|---|---|---|---|
| A431 | 298 | 20 | 4 | >1000 | >1000 |
| HCC827 | 12 | <5 | 78 | 10-100 | 10-100 |
| H1975 | >5000 | 196 | 13 | 100-500 | 100-500 |

In some embodiments, a provided compound is at least 50, at least 45 times, at least 40, at least 35, at least 30, at least 25, or at least 20 times more potent for at least one mutation of EGFR as compared to WT EGFR, as determined by the biochemical assay described in detail in Example 24, infra. In certain embodiments, a provided compound is at least 20, at least 15, or at least 10 times more potent for at least one mutation of EGFR as compared to WT EGFR, as determined by the cellular assay described in detail in Example 26, infra.

In some embodiments, a provided compound is at least 50, at least 45 times, at least 40, at least 35, at least 30, at least 25, or at least 20 times more potent for at least one deletion mutation of EGFR as compared to WT EGFR, as determined by the biochemical assay described in detail in Example 24, infra. In certain embodiments, a provided compound is at least 20, at least 15, or at least 10 times more potent for at least one deletion mutation of EGFR as compared to WT EGFR, as determined by the cellular assay described in detail in Example 26, infra.

In some embodiments, a provided compound is at least 50, at least 45 times, at least 40, at least 35, at least 30, at least 25, or at least 20 times more potent for L858R and/or T790M mutation of EGFR as compared to WT EGFR, as determined by the biochemical assay described in detail in Example 24, infra. In certain embodiments, a provided compound is at least 20, at least 15, or at least 10 times more potent for L858R and/or T790M mutation of EGFR as compared to WT EGFR, as determined by the cellular assay described in detail in Example 26, infra.

In some embodiments, a provided compound is at least 20, at least 15, or at least 10 times more potent for double mutant in H1975 cells, as compared to WT EGFR, in the signaling assay described in detail in Example 25.

In certain embodiments, a provided compound inhibits at least one mutation of EGFR selectively as compared to WT EGFR and as compared to other protein kinases (e.g., ErbB2, ErbB4, a TEC-kinase, and/or JAK3). It will be appreciated that the acrylamide moiety, depicted in formula I, is a warhead group for covalently binding to a key cysteine residue in the binding domain of at least one mutation of EGFR selectively as compared to WT EGFR and other protein kinases. Protein kinases having a cysteine residue in the binding domain are known to one of ordinary skill in the art. Such protein kinases having a cysteine residue in the binding domain include the TEC-family of protein kinases (including TEC, BTK, ITK, BMX, JAK3, and RLK). In certain embodiments, the cysteine residue is conserved across a protein kinase sub-family, such as ErbB1 (commonly referred to as EGFR), ErbB2, and ErbB4.

Without wishing to be bound by any particular theory, it is believed that provided compounds irreversibly inhibit (i.e., covalently modify) at least one mutation of EGFR selectively as compared to WT EGFR and other protein kinases. In some embodiments, a provided compound irreversibly inhibits at least one mutation of EGFR selectively as compared to at least one protein kinase selected from ErbB1, ErbB2, ErbB4, TEC, BTK, ITK, BMX, JAK3, or RLK.

Notwithstanding, in certain embodiments, provided compounds do not appreciably inhibit, either reversibly or irreversibly, other protein kinases. In some embodiments, a provided compound is selective for inhibiting at least one mutant of EGFR as compared to off-target protein kinases thereby avoiding effects and toxicities associated with inhibition thereof.

3. Uses, Formulation and Administration

Pharmaceutically Acceptable Compositions

According to another embodiment, the invention provides a composition comprising a compound of this invention, or a pharmaceutically acceptable salt thereof, and a pharmaceutically acceptable carrier, adjuvant, or vehicle. An amount of compound in a composition of this invention is such that is effective to measurably inhibit a protein kinase, particularly to inhibit at least one mutant of EGFR selectively as compared to WT EGFR, in a biological sample or in a patient. In certain embodiments, an at least one mutant of EGFR is T790M. In certain embodiments, the at least one mutant of EGFR is a deletion mutation of EGFR. In some embodiments, the at least one mutation of EGFR is L858R and/or T790M.

In certain embodiments, an amount of compound in a provided composition is such that is effective to measurably inhibit at least one mutation of EGFR selectively as compared to WT EGFR and other protein kinases (e.g., ErbB2, ErbB4, a TEC-kinase, and/or JAK3).

In certain embodiments, the amount of compound in a provided composition is such that is effective to measurably inhibit at least one mutant of EGFR selectively as compared to WT EGFR, in a biological sample or in a patient. In certain embodiments, a composition of this invention is formulated for administration to a patient in need of such composition. In some embodiments, a composition of this invention is formulated for oral administration to a patient.

In certain embodiments, the amount of compound in a provided composition is such that is effective to measurably inhibit at least one mutant of EGFR selectively as compared to WT EGFR and other protein kinases (e.g., ErbB2, ErbB4, a TEC-kinase, and/or JAK3), in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutically acceptable compositions of this invention are formulated for oral administration.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the selective inhibition of at least one mutant of EGFR as compared to WT EGFR. In certain embodiments, an at least one mutant of EGFR is T790M. In certain embodiments, the at least one mutant of EGFR is a deletion mutation of EGFR, an activating mutation of EGFR, or a combination thereof. In some embodiments, the at least one mutation of EGFR is L858R and/or T790M.

In certain embodiments, a provided compound selectively inhibits (a) at least one activating mutation, (b) T790M and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

In some embodiments, the at least one mutation of EGFR is L858R and/or T790M.

The activity of a compound utilized in this invention as a selective inhibitor of at least one mutant of EGFR as compared to WT EGFR, may be assayed in vitro, in vivo or in a cell line. In vitro assays include assays that determine inhibition of the phosphorylation activity and/or the subsequent functional consequences, or ATPase activity of activated EGFR (WT or mutant). Alternate in vitro assays quantitate the ability of the inhibitor to bind to EGFR (WT or mutant). Inhibitor binding may be measured by radiolabeling the inhibitor prior to binding, isolating the inhibitor/EGFR (WT or mutant) complex and determining the amount of radiolabel bound. Alternatively, inhibitor binding may be determined by running a competition experiment where new inhibitors are incubated with EGFR (WT or mutant) bound to known radioligands. Detailed conditions for assaying a compound utilized in this invention as an inhibitor of EGFR (WT or mutant), are set forth in the Examples below.

Protein tyrosine kinases are a class of enzymes that catalyze the transfer of a phosphate group from ATP or GTP to a tyrosine residue located on a protein substrate. Receptor tyrosine kinases act to transmit signals from the outside of a cell to the inside by activating secondary messaging effectors via a phosphorylation event. A variety of cellular processes are promoted by these signals, including proliferation, carbohydrate utilization, protein synthesis, angiogenesis, cell growth, and cell survival.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of at least one mutant of EGFR and are therefore useful for treating one or more disorders associated with activity of one of more EGFR mutants (e.g., a deletion mutation, an activating mutation, or combination thereof). Thus, in certain embodiments, the present invention provides a method for treating a mutant EGFR-mediated disorder comprising the step of administering to a patient in need thereof a compound of the present invention, or pharmaceutically acceptable composition thereof.

As used herein, the term "mutant EGFR-mediated" disorders or conditions as used herein means any disease or other deleterious condition in which at least one mutant of EGFR is known to play a role. In certain embodiments, an at least one mutant of EGFR is T790M. In some embodiments, the at least one mutant of EGFR is a deletion mutation. In certain embodiments, the at least one mutant of EGFR is an activating mutation. In some embodiments, the at least one mutant of EGFR is L858R and/or T790M. In certain embodiments, a provided compound selectively inhibits (a) at least one activating mutation, (b) T790M, and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

Accordingly, another embodiment of the present invention relates to treating or lessening the severity of one or more diseases in which at least one mutant of EGFR is known to play a role. Specifically, the present invention relates to a method of treating or lessening the severity of a disease or condition selected from a proliferative disorder, wherein said method comprises administering to a patient in need thereof a compound or composition according to the present invention.

In some embodiments, the present invention provides a method for treating or lessening the severity of one or more disorders selected from a cancer. In some embodiments, the cancer is associated with a solid tumor. In certain embodiments, the cancer is breast cancer, glioblastoma, lung cancer, cancer of the head and neck, colorectal cancer, bladder cancer, or non-small cell lung cancer. In some embodiments, the present invention provides a method for treating or lessening the severity of one or more disorders selected from squamous cell carcinoma, salivary gland carcinoma, ovarian carcinoma, or pancreatic cancer.

In certain embodiments, the present invention provides a method for treating or lessening the severity of neurofibromatosis type I (NF1), neurofibromatosis type II (NF2) Schwann cell neoplasms (e.g. MPNST's), or Schwannomas.

The compounds and compositions, according to the method of the present invention, may be administered using any amount and any route of administration effective for treating or lessening the severity of a cancer. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg or from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, terminal (heat) sterilization, or sterilization via ionizing radiationor by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like. In some embodiments, a solid composition is a liquid filled hard gelatin capsule or solid dispersion.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to another embodiment, the invention relates to a method of inhibiting at least one mutant of EGFR (e.g., a deletion mutation, an activating mutation, a resistant mutation, or combination thereof) activity in a biological sample comprising the step of contacting said biological sample with a compound of this invention, or a composition comprising said compound. In certain embodiments, the invention relates to a method of irreversibly inhibiting at least one mutant of EGFR (e.g., a deletion mutation, an activating mutation, or combination thereof) activity in a biological sample comprising the step of contacting said biological sample with a compound of this invention, or a composition comprising said compound.

In certain embodiments, a provided compound selectively inhibits in a biological sample (a) at least one activating mutation, (b) T790M, and (c) is sparing as to WT. In some embodiments, an at least one activating mutation is a deletion mutation. In some embodiments, an at least one activating mutation is a point mutation. In some embodiments, an activating mutation is delE746-A750. In some embodiments, an activating mutation is L858R. In some embodiments, an activating mutation is G719S.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of at least one mutant of EGFR (e.g., a deletion mutation, an activating mutation, a resistant mutation, or combination thereof) activity in a biological sample is useful for a variety of purposes that are known to one of skill in the art. Examples of such purposes include, but are not limited to, blood transfusion, organ transplantation, biological specimen storage, and biological assays.

Another embodiment of the present invention relates to a method of inhibiting at least one mutant of EGFR (e.g., a deletion mutation, an activating mutation, a resistant mutation, or combination thereof) activity in a patient comprising the step of administering to said patient a compound of the present invention, or a composition comprising said compound. In certain embodiments, the present invention provides a method for inhibiting (a) at least one activating mutation, (b) T790M in a patient, and (c) is sparing as to WT, wherein said method comprises administering to the patient a provided compound, or composition thereof. In some embodiments, an at least one activating mutation is a deletion mutation. In some embodiments, the present invention provides a method for inhibiting at least one mutant of EGFR in a patient, wherein an at least one activating mutation is a point mutation. In some embodiments, the present invention provides a method for inhibiting at least one mutant of EGFR in a patient, wherein an activating mutation is delE746-A750. In some embodiments, the present invention provides a method for inhibiting at least one mutant of EGFR in a patient, wherein an activating mutation is L858R. In some embodiments, the present invention provides a method for inhibiting at least one mutant of EGFR in a patient, wherein an activating mutation is G719S.

According to another embodiment, the invention relates to a method of inhibiting at least one mutant of EGFR (e.g., a deletion mutation, an activating mutation, a resistant mutation, or combination thereof) activity in a patient comprising the step of administering to said patient a compound of the present invention, or a composition comprising said compound. According to certain embodiments, the invention relates to a method of irreversibly inhibiting at least one mutant of EGFR activity (e.g., a deletion mutation, an activating mutation, a resistant mutation, or combination thereof) in a patient comprising the step of administering to said patient a compound of the present invention, or a composition comprising said compound. In certain embodiments, the present invention provides a method for irreversibly inhibiting (a) at least one activating mutation and (b) T790M in a patient, and (c) is sparing as to WT, wherein said method comprises administering to the patient a provided compound, or composition thereof. In some embodiments, an at least one activating mutation is a deletion mutation. In some embodiments, an at least one activating mutation is a point mutation. In some embodiments, the present invention provides a method for irreversibly inhibiting at least one mutant of EGFR in a patient, wherein an activating mutation is delE746-A750. In some embodiments, the present invention provides a method for irreversibly inhibiting at least one mutant of EGFR in a patient, wherein an activating mutation is L858R. In some embodiments, the present invention provides a method for irreversibly inhibiting at least one mutant of EGFR in a patient, wherein an activating mutation is G719S.

In other embodiments, the present invention provides a method for treating a disorder mediated by one or more of at least one mutant of EGFR (e.g., a deletion mutation, an activating mutation, a resistant mutation, or combination thereof) in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, camptothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention may also be combined with include, without limitation: treatments for Alzheimer's Disease such as donepezil hydrochloride (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate)(Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Compound numbers utilized in the Examples below correspond to compound numbers set forth in Table 1, supra.

Provided compounds are prepared according to methods known to one of ordinary skill in the art and include methods described in detail in US 20100029610, published Feb. 4, 2010, the entirety of which is hereby incorporated herein by reference.

EXAMPLE 1

Compound I-11, N-(3-(5-(trifluoromethyl)-2-(2,3,4-trimethoxyphenylamino)pyrimidin-4-ylamino)phenyl)acrylamide)

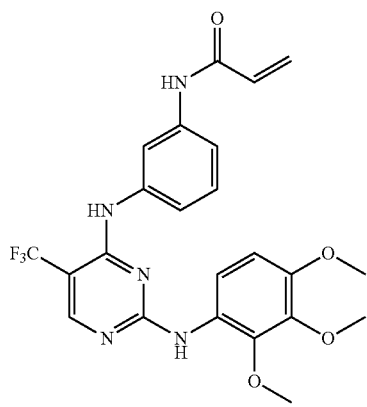 [SMILES: C=CC(=O)Nc1cccc(Nc2nc(Nc3ccc(OC)c(OC)c3OC)ncc2C(F)(F)F)c1]

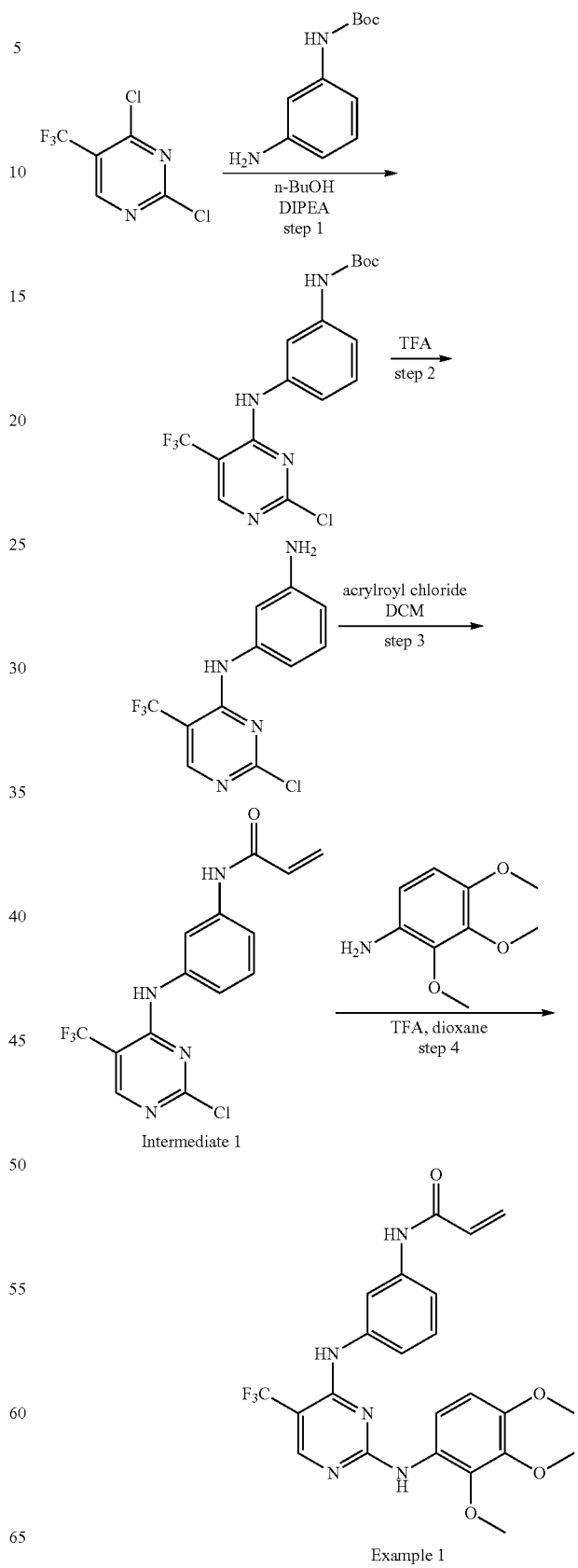

Example 1

Step 1:

In a 25 mL 3-neck RBF previously equipped with a magnetic stirrer, Thermo pocket and $CaCl_2$ guard tube, N-Boc-1,3-diaminobenzene (0.96 g) and n-butanol (9.00 mL) were charged. Reaction mixture was cooled to 0° C. 2,4-Dichloro-5-trifluoromethylpyrimidine (1.0 g) was added dropwise to the above reaction mixture at 0° C. The DIPEA (0.96 mL) was dropwise added to the above reaction mixture at 0° C. and the reaction mixture was stirred for 1 hr at 0° C. to 5° C. Finally the reaction mixture was allowed to warm to room temperature. Reaction mixture was stirred for another 4 hrs at room temperature. Completion of reaction was monitored by TLC using hexane:ethyl acetate (7:3). The solid precipitated out was filtered off and washed with 1-butanol (2 mL). Solid was dried under reduced pressure at 40° C. for 1 hr. $^1$H-NMR (DMSO-d6, 400 MHz) δ 1.48 (S, 9H), 7.02 (m, 1H), 7.26 (m, 2H), 7.58 (S, 1H), 8.57 (S, 1H), 9.48 (S, 1H), 9.55 (S, 1H).

Step 2:

To the above crude (3.1 g) in DCM (25 mL) was added TFA (12.4 mL) slowly at 0° C. The reaction mixture was allowed to warm to room temperature. Reaction mixture was stirred for another 10 min at room temperature. The crude was concentrated under reduced pressure.

Step 3:

The concentrated crude was dissolved in DIPEA (2.0 mL) and DCM (25 mL), and then cooled to −30° C. To the reaction mixture was slowly added acryloyl chloride (0.76 g) at −30° C. The reaction mass was warmed to room temperature stirred at room temperature for 1.0 hr. The reaction was monitored on TLC using hexane:ethyl acetate (7:3) as mobile phase. Reaction got completed after 1 hr. $^1$H-NMR (DMSO-d6, 400 MHz) δ 5.76 (dd, J=2.0, 10.0 Hz, 1H), 6.24 (dd, J=2.0, 17.2 Hz, 1H), 6.48 (m, 1H), 7.14 (d, J=8.8 Hz, 1H), 7.37 (t, J=8.0 Hz, 1H), 7.94 (S, 1H), 8.59 (S, 1H), 9.60 (S, 1H), 10.26 (S, 1H).

Step 4:

To obtain the example 1, a mixture of the intermediate 1 (16 mg) and 2,3,4-trimethoxyaniline (20 uL) in dioxane (1.0 mL) with catalytic trifluoroacetic acid was stirred overnight at 50° C. The crude was concentrated under reduced pressure and purified using HPLC (TFA modifier) to give the title compound (17 mg) as a TFA salt. $^1$H-NMR (DMSO-d6, 400 MHz) δ 10.2 (S, 1H), 8.94 (br, 1H), 8.52 (br, 1H), 8.34 (S, 1H), 7.78 (S, 1H), 7.49 (d, J=7.8 Hz, 1H), 7.29 (m, 2H), 7.14 (br, 1H), 6.43 (dd, J=10.1, 16.8 Hz, 1H) 6.24 (dd, J=1.8, 16.8 Hz, 1H), 5.75 (dd, J=1.8, 10.1 Hz, 1H), 3.74 (S, 3H), 3.71 (S, 3H), 3.70 (S, 3H); calculated mass for $C_{23}H_{22}F_3N_5O_4$: 489.2, found: 490.0 (M+H$^+$).

EXAMPLE 2

Compound I-12, N-(3-(5-chloro-2-(2-methoxyphenylamino)pyrimidin-4-yloxy)phenyl)acrylamide)

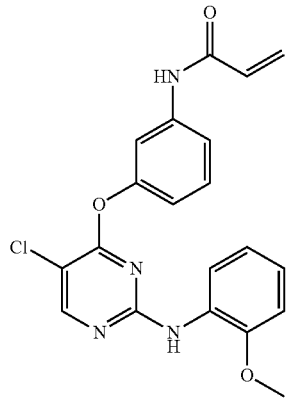 [SMILES: C=CC(=O)Nc1cccc(Oc2nc(Nc3ccccc3OC)ncc2Cl)c1]

Compound I-12 was prepared via a similar route as described in Example 1 by using N-Boc-3-aminophenol and 2,4,5-trichloropyrimidine in Step 1 and 2-methoxyaniline in Step 4. Calculated mass for $C_{20}H_{17}ClN_4O_3$: 396.1, found: 397.0 (M+H$^+$).

EXAMPLE 3

Compound I-10, N-(3-(5-(trifluoromethyl)-2-(2,3,4-trimethoxyphenylamino)pyrimidin-4-yloxy)phenyl)acrylamide)

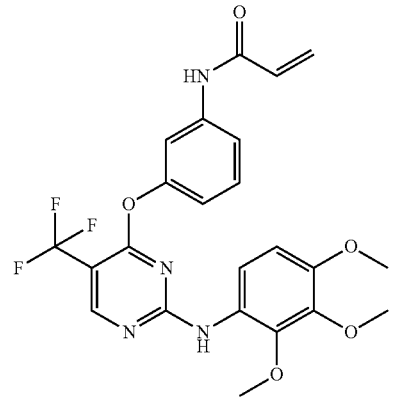 [SMILES: C=CC(=O)Nc1cccc(Oc2nc(Nc3ccc(OC)c(OC)c3OC)ncc2C(F)(F)F)c1]

Compound I-10 was prepared via a similar route as described in Example 1 by using N-Boc-3-aminophenol and 2,4-dichloro-5-trifluoromethylpyrimidine in Step 1 and 2,3,4-trimethoxyaniline in Step 4. $^1$H-NMR (DMSO-d6, 400 MHz) δ 10.32 (S, 1H), 9.08 (S, 1H), 8.58 (S, 1H), 7.65 (S, 1H), 7.52 (d, J=8.4 Hz, 1H), 7.4 (t, J=8.0 Hz, 1H), 7.03 (m, 1H), 6.97 (d, J=7.6 Hz, 1H), 6.43 (dd, J=10.0, 16.8 Hz, 1H), 6.27 (dd, J=2.0, 16.8 Hz, 1H), 5.78 (dd, J=2.0, 10.0 Hz, 1H), 3.74 (S, 3H), 3.71 (S, 3H), 3.70 (S, 3H); calculated mass for $C_{23}H_{21}F_3N_4O_5$: 490.1, found: 491.5 (M+H$^+$).

EXAMPLE 4

Compound I-9, N-(3-(2-(2,4-dimethoxyphenylamino)-5-(trifluoromethyl)pyrimidin-4-yloxy)phenyl)acrylamide)

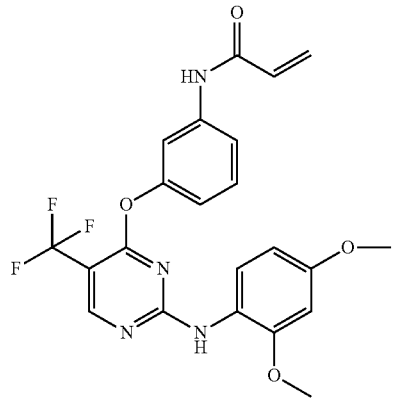 [SMILES: C=CC(=O)Nc1cccc(Oc2nc(Nc3ccc(OC)cc3OC)ncc2C(F)(F)F)c1]

Compound I-9 was prepared via a similar route as described in Example 1 by using N-Boc-3-aminophenol and 2,4-dichloro-5-trifluoromethylpyrimidine in Step 1 and 2,4-dimethoxyaniline in Step 4. $^1$H-NMR (DMSO-d6, 400 MHz) δ 10.3 (S, 1H), 8.92 (S, 1H), 8.55 (br, 1H), 7.64 (S, 1H), 7.54

(d, J=7.2 Hz, 1H), 7.41 (br, 1H), 7.20 (d, J=8.4 Hz, 1H), 6.96 (br, 1H), 6.54 (br, 1H), 6.43 (dd, J=10.0, 17.2 Hz, 1H), 6.27 (dd, J=2.0, 17.2 Hz, 1H), 5.79 (dd, J=2.0, 10.0 Hz, 1H), 3.71 (S, 6H); calculated mass for $C_{22}H_{19}F_3N_4O_4$: 460.1, found: 461.4 (M+H$^+$).

EXAMPLE 5

Compound I-8, N-(3-(5-bromo-2-(2,3,4-trimethoxyphenylamino)pyrimidin-4-yloxy)phenyl)acrylamide)

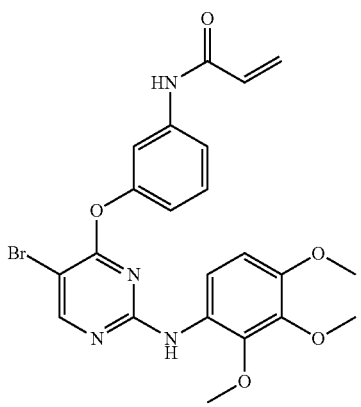

Compound I-8 was prepared via a similar route as described in Example 1 by using N-Boc-3-aminophenol and 2,4-dichloro-5-bromopyrimidine in Step 1 and 2,3,4-trimethoxyaniline in Step 4. $^1$H-NMR (DMSO-d6, 400 MHz) δ 10.34 (S, 1H), 8.45 (S, 1H), 8.42 (S, 1H), 7.63 (S, 1H), 7.55 (d, J=8.0 Hz, 1H), 7.42 (t, J=8.0 Hz, 1H), 7.09 (d, J=9.2 Hz, 1H), 6.98 (dd, J=1.2, 7.6 Hz, 1H), 6.40-6.47 (m, 2H), 6.26 (dd, J=2.0, 17.2 Hz, 1H), 5.78 (dd, J=2.0, 10.0 Hz, 1H), 3.72 (S, 3H), 3.71 (s, 3H), 3.70 (S, 3H); calculated mass for $C_{22}H_{21}BrN_4O_5$: 500.1, found: 501.2 (M+H$^+$).

EXAMPLE 6

Compound I-13, N-(3-(5-bromo-2-(2,4-dimethoxyphenylamino)pyrimidin-4-yloxy)phenyl)acrylamide)

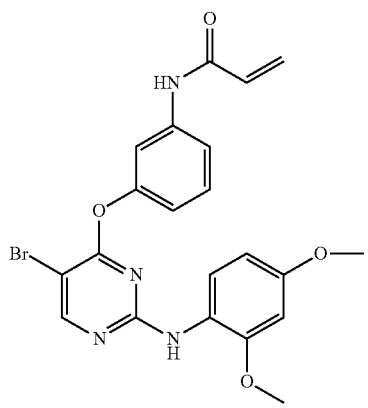

Compound I-13 was prepared via a similar route as described in Example 1 by using N-Boc-3-aminophenol and 2,4-dichloro-5-bromopyrimidine in Step 1 and 2,4-dimethoxyaniline in Step 4. Calculated mass for $C_{21}H_{19}BrN_4O_4$: 470.1, found: 471.2 (M+H$^+$).

EXAMPLE 7

Compound I-5, N-(3-(5-bromo-2-(2,3,4-trimethoxyphenylamino)pyrimidin-4-ylamino)phenyl)acrylamide)

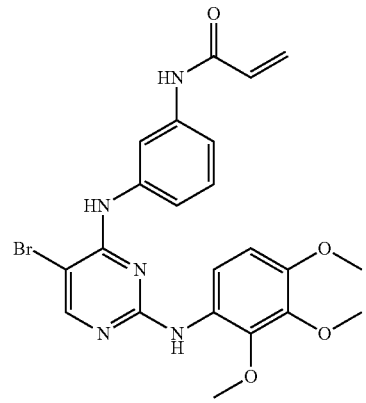 [SMILES: C=CC(=O)Nc1cccc(Nc2nc(Nc3ccc(OC)c(OC)c3OC)ncc2Br)c1]

Compound I-5 was prepared via a similar route as described in Example 1 by using N-Boc-1,3-diaminobenzene and 2,4-dichloro-5-bromopyrimidine in Step 1 and 2,3,4-trimethoxyaniline in Step 4. $^1$H-NMR (DMSO-d6, 400 MHz) δ 10.15 (S, 1H), 8.63 (S, 1H), 8.17 (S, 1H), 7.94 (S, 1H), 7.89 (S, 1H), 7.52 (d, J=9.2 Hz, 1H), 7.43 (m, 1H), 7.24 (m, 2H), 6.51 (m, 1H), 6.44 (dd, J=10.0, 17.2 Hz, 1H), 6.26 (dd, J=2.0, 17.2 Hz, 1H), 5.76 (dd, J=2.0, 10.0 Hz, 1H), 3.77 (S, 3H), 3.73 (S, 3H), 3.72 (S, 3H); calculated mass for $C_{22}H_{22}BrN_5O_4$: 499.1, found: 500.1 (M+H$^+$).

EXAMPLE 8

Compound I-14, N-(3-(5-bromo-2-(2,3-dimethoxyphenylamino)pyrimidin-4-ylamino)phenyl)acrylamide)

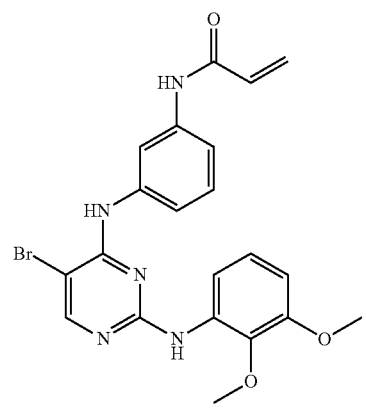 [SMILES: C=CC(=O)Nc1cccc(Nc2nc(Nc3cccc(OC)c3OC)ncc2Br)c1]

Compound I-14 was prepared via a similar route as described in Example 1 by using N-Boc-1,3-diaminobenzene and 2,4-dichloro-5-bromopyrimidine in Step 1 and 2,3- dimethoxyaniline in Step 4. Calculated mass for C$_{21}$H$_{20}$BrN$_5$O$_3$: 469.1, found: 470.3 (M+H$^+$).

EXAMPLE 9

Compound I-15, N N-(3-(5-chloro-2-(2,4-dimethoxyphenylamino)pyrimidin-4-yloxy)phenyl)acrylamide)

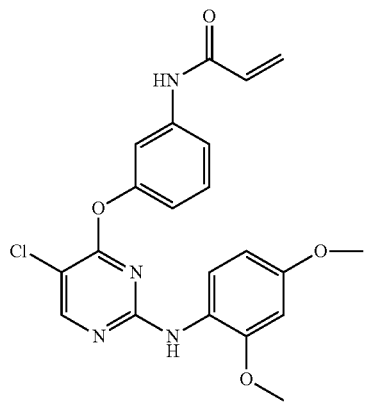 [SMILES: C=CC(=O)Nc1cccc(Oc2nc(Nc3ccc(OC)cc3OC)ncc2Cl)c1]

Compound I-15 was prepared via a similar route as described in Example 1 by using N-Boc-3-aminophenol and 2,4,5-trichloropyrimidine in Step 1 and 2,4-dimethoxyaniline in Step 4. Calculated mass for C$_{21}$H$_{19}$ClN$_4$O$_4$: 426.1, found: 427.3 (M+H$^+$).

EXAMPLE 10

Compound I-7, N-(3-(5-chloro-2-(2,3,4-trimethoxyphenylamino)pyrimidin-4-yloxy)phenyl)acrylamide)

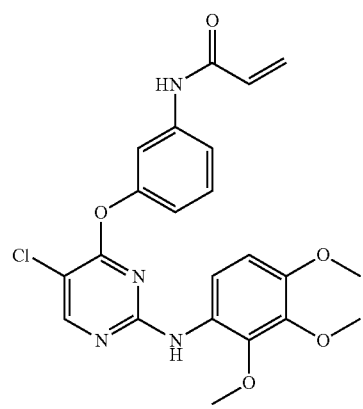 [SMILES: C=CC(=O)Nc1cccc(Oc2nc(Nc3ccc(OC)c(OC)c3OC)ncc2Cl)c1]

Compound I-7 was prepared via a similar route as described in Example 1 by using N-Boc-3-aminophenol and 2,4,5-trichloropyrimidine in Step 1 and 2,3,4-trimethoxyaniline in Step 4. $^1$H-NMR (DMSO-d6, 400 MHz) δ 10.36 (S, 1H), 8.44 (S, 1H), 8.40 (S, 1H), 7.65 (1H, s), 7.55 (d, J=8.4 Hz, 1H), 7.43 (t, J=8.0 Hz, 1H), 7.09 (d, J=9.2 Hz, 1H), 6.99 (d, J=8.4 Hz, 1H), 6.43-6.47 (m, 2H), 6.27 (dd, J=2.0, 16.8 Hz, 1H), 5.79 (dd, J=2.0, 11.6 Hz, 1H), 3.71 (S, 3H), 3.70 (S, 3H), 3.69 (S, 3H); calculated mass for C$_{22}$H$_{21}$ClN$_4$O$_5$: 456.1, found: 457.3 (M+H).

EXAMPLE 11

Compound I-4, N-(3-(5-chloro-2-(2,3,4-trimethoxyphenylamino)pyrimidin-4-ylamino)phenyl)acrylamide)

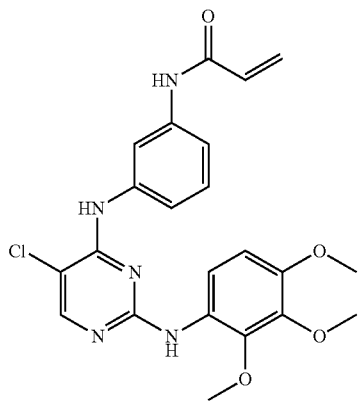 [SMILES: C=CC(=O)Nc1cccc(Nc2nc(Nc3ccc(OC)c(OC)c3OC)ncc2Cl)c1]

Compound I-4 was prepared via a similar route as described in Example 1 by using N-Boc-1,3-diaminobenzene and 2,4,5-trichloropyrimidine in Step 1 and 2,3,4-trimethoxyaniline in Step 4. $^1$H-NMR (DMSO-d6, 400 MHz) δ 10.16 (S, 1H), 8.9 (S, 1H), 8.1 (S, 1H), 8.0 (S, 1 H), 7.9 (S, 1H), 7.49 (d, J=8.4 Hz, 1H), 7.37 (d, J=6.8 Hz, 1H), 7.22-7.29 (m, 2H), 6.45-6.55 (m, 2H), 6.26 (dd, J=1.7, 17.0 Hz, 1H), 5.75 (dd, J=1.7, 9.6 Hz, 1H), 3.72 (S, 3H), 3.68 (S, 3H), 3.67 (S, 3H); calculated mass for C$_{22}$H$_{22}$ClN$_5$O$_4$: 455.1, found: 456.3 (M+H$^+$).

EXAMPLE 12

Compound I-3, N-(3-(2-(2,4-dimethoxyphenylamino)-5-(trifluoromethyl)pyrimidin-4-ylamino)phenyl)acrylamide)

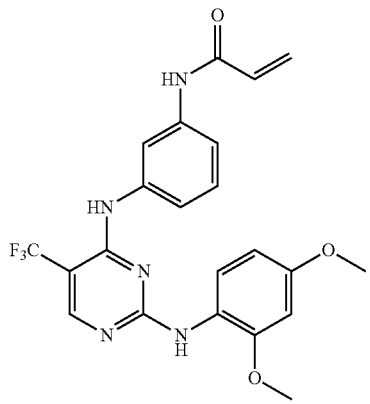 [SMILES: C=CC(=O)Nc1cccc(Nc2nc(Nc3ccc(OC)cc3OC)ncc2C(F)(F)F)c1]

Compound I-3 was prepared via a similar route as described in Example 1 by using N-Boc-1,3-diaminobenzene and 2,4-dichloro-5-trifluoromethylpyrimidine in Step 1 and 2,4-dimethoxyaniline in Step 4. ¹H-NMR (DMSO-d6, 400 MHz) δ 10.2 (S, 1H), 9.11 (br, 1H), 8.62 (br, 1H), 8.34 (br, 1H), 7.78 (S, 1H), 7.46 (dd, J=7.8, 16.5 Hz, 2H), 7.28 (t, J=8.0 Hz, 1 H), 7.14 (br, 1H), 6.57 (d, J=1.8 Hz, 1H), 6.43 (dd, J=10.1, 16.9 Hz, 1H), 6.24 (dd, J=1.8, 16.9 Hz, 1H), 5.74 (dd, J=1.8, 10.1, 1H), 3.76 (S, 3H), 3.70 (S, 3H); calculated mass for $C_{22}H_{20}F_3N_5O_3$: 459.2, found: 460.2 (M+H⁺).

EXAMPLE 13

Compound I-16, N-(3-(2-(2,3-dimethoxyphenylamino)-5-(trifluoromethyl)pyrimidin-4-ylamino)phenyl)acrylamide)

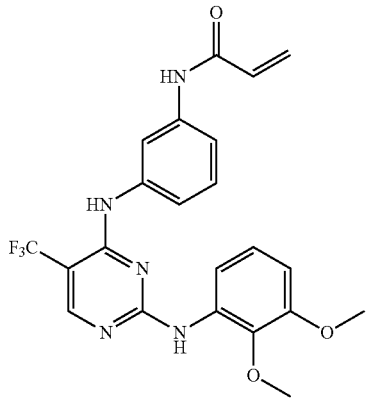

Compound I-16 was prepared via a similar route as described in Example 1 by using N-Boc-1,3-diaminobenzene and 2,4-dichloro-5-trifluoromethylpyrimidine in Step 1 and 2,3-dimethoxyaniline in Step 4. Calculated mass for $C_{22}H_{20}F_3N_5O_3$: 459.2, found: 460.2 (M+H⁺).

EXAMPLE 14

Compound I-2, N-(3-(2-(2-methoxyphenylamino)-5-(trifluoromethyl)pyrimidin-4-yloxy)phenyl)acrylamide)

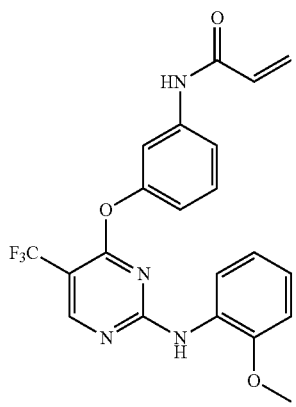 [SMILES: C=CC(=O)Nc1cccc(Oc2nc(Nc3ccccc3OC)ncc2C(F)(F)F)c1]

Compound I-2 was prepared via a similar route as described in Example 1 by using N-Boc-3-aminophenol and 2,4-dichloro-5-trifluoromethylpyrimidine in Step 1 and 2-methoxyaniline in Step 4. ¹H-NMR (DMSO-d6, 400 MHz) δ 10.3 (S, 1H), 8.87 (S, 1H), 8.62 (S, 1H), 7.67 (t, J=2.3 Hz, 1H), 7.50 (d, J=9.2 Hz, 1H), 7.41 (t, J=8.3 Hz, 2H), 7.02 (m, 1 H), 6.97 (t, J=7.3 Hz, 1H), 6.65 (br, 1H), 6.41 (dd, J=10.1, 17.0 Hz, 1H), 6.25 (dd, J=2.3, 17.0 Hz, 1H), 5.77 (dd, J=2.3, 10.1 Hz, 1H), 3.74 (S, 3H); calculated mass for $C_{21}H_{17}F_3N_4O_3$: 430.1, found: 431.1 (M+H⁺).

EXAMPLE 15

Compound I-1, N-(3-(2-(2-methoxyphenylamino)-5-(trifluoromethyl)pyrimidin-4-ylamino)phenyl)acrylamide)

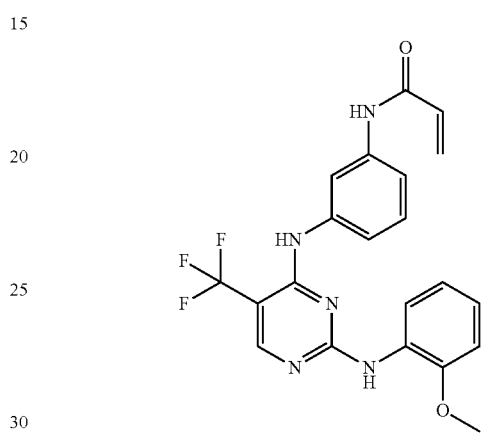

Compound I-1 was prepared via similar route as described in Example 1 by using N-Boc-1,3-diaminobenzene and 2,4-dichloro-5-trifluoromethylpyrimidine in Step 1 and 2-methoxyaniline in Step 4. ¹H-NMR (DMSO-d6, 400 MHz) δ 10.2 (S, 1H), 9.1 (S, 1H), 8.41 (S, 1H), 8.38 (S, 1H), 7.8 (S, 1H), 7.7 (d, J=7.8 Hz, 1H), 7.5 (d, J=8.2 Hz, 1H), 7.3 (t, J=8.2 Hz, 1H), 7.1 (d, J=8.2 Hz, 1H), 6.97 (S, 2H), 6.62 (br, 1H), 6.41 (dd, J=10.1, 17.0 Hz, 1H), 6.24 (d, J=17.0 Hz, 1H), 5.74 (d, J=10.1 Hz, 1H), 3.79 (S, 3H); calculated mass for $C_{21}H_{18}F_3N_5O_2$: 429.1. found: 430.0 (M+H⁺).

EXAMPLE 16

Compound I-18, N-(3-(5-chloro-2-(2-methoxyphenylamino)pyrimidin-4-ylamino)phenyl)acrylamide)

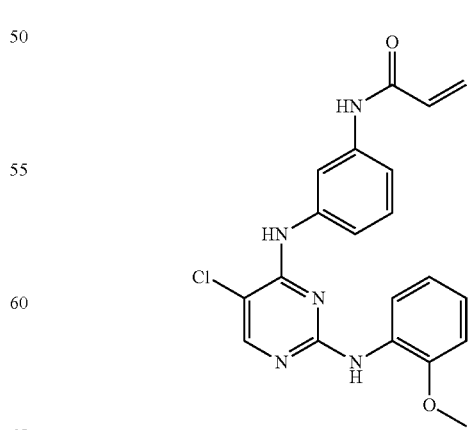

Compound I-18 was prepared via similar route as described in Example 1 by using N-Boc-1,3-diaminobenzene and 2,4,5-trichloropyrimidine in Step 1 and 2-methoxyaniline in Step 4. Calculated mass for $C_{20}H_{18}ClN_5O_2$: 395.1. found: 396.1 (M+H$^+$).

EXAMPLE 17

Compound I-19, N-(3-(5-fluoro-2-(2-methoxyphenylamino)pyrimidin-4-yloxy)phenyl)acrylamide)

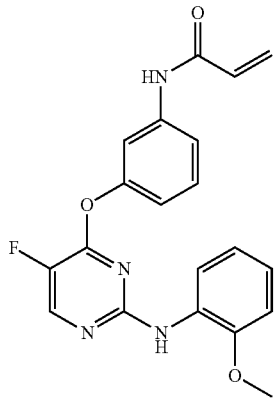 [SMILES: C=CC(=O)Nc1cccc(Oc2nc(Nc3ccccc3OC)ncc2F)c1]

Compound I-19 was prepared via similar route as described in Example 1 by using N-Boc-3-aminophenol and 2,4-dichloro-5-fluoropyrimidine in Step 1 and 2-methoxyaniline in Step 4. Calculated mass for $C_{20}H_{17}FN_4O_3$: 380.1. found: 381.4 (M+H$^+$).

EXAMPLE 18

Compound I-6, N-(3-(5-bromo-2-(2,3-dimethoxyphenylamino)pyrimidin-4-yloxy)phenyl)acrylamide)

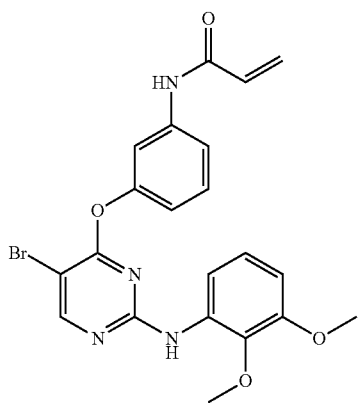

Compound I-6 was prepared via similar route as described in Example 1 by using N-Boc-3-aminophenol and 2,4-dichloro-5-bromopyrimidine in Step 1 and 2,3-dimethoxyaniline in Step 4. $^1$H-NMR (DMSO-d6, 400 MHz) δ 10.35 (S, 1H), 8.53 (S, 1H), 8.35 (S, 1H), 7.69 (S, 1 H), 7.55 (m, 1H), 7.46 (m, 1H). 7.11 (dd, J=6.4 Hz, 1H), 6.96 (d, J=7.2 Hz, 1H), 6.64 (m, 2 H), 6.43 (dd, J=10.0, 17.0 Hz, 1H), 6.26 (dd, J=2.0, 17.0 Hz, 1H), 5.77 (dd, J=2.0, 10.0 Hz, 1H), 3.71 (S, 3H), 3.65 (S, 3H); calculated mass for $C_{21}H_{19}BrN_4O_4$: 470.1. found: 471.3 (M+H).

EXAMPLE 19

Compound I-20, N-(3-(5-bromo-2-(2,4-dimethoxyphenylamino)pyrimidin-4-ylamino)phenyl)acrylamide)

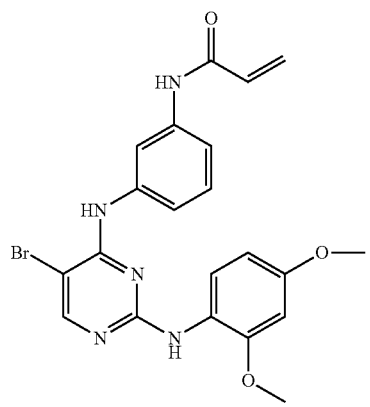

Compound I-20 was prepared via similar route as described in Example 1 by using N-Boc-1,3-diaminobenzene and 2,4-dichloropyrimidine in Step 1 and 2,4-dimethoxyaniline in Step 4. Calculated mass for $C_{21}H_{20}BrN_5O_3$: 469.1. found: 469.9 (M+H$^+$).

EXAMPLE 20

Compound I-21, N-(3-(5-chloro-2-(2,4-dimethoxyphenylamino)pyrimidin-4-ylamino)phenyl)acrylamide)

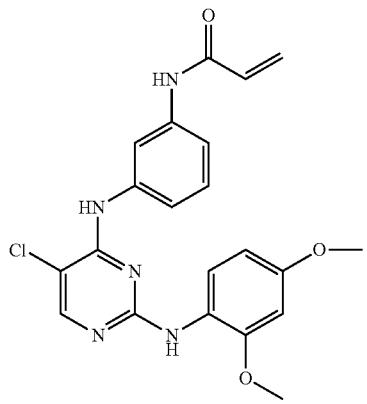

Compound I-21 was prepared via similar route as described in Example 1 by using N-Boc-1,3-diaminobenzene and 2,4,5-trichloropyrimidine in Step 1 and 2,4-dimethoxyaniline in Step 4. Calculated mass for $C_{21}H_{20}ClN_5O_3$: 425.1. found: 426.3 (M+H$^+$).

EXAMPLE 21

Compound I-22, N-(3-(5-bromo-2-(2-methoxyphenylamino)pyrimidin-4-ylamino)phenyl)acrylamide)

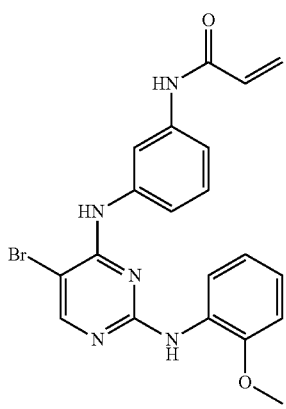

Compound I-22 was prepared via similar route as described in Example 1 by using N-Boc-1,3-diaminobenzene and 2,4-dichloro-5-bromopyrimidine in Step 1 and 2-methoxyaniline in Step 4. Calculated mass for $C_{20}H_{18}BrN_5O_2$: 439.1. found: 440.1 (M+H$^+$).

EXAMPLE 22

Compound I-23, N-(3-(2-(2,3-dimethoxyphenylamino)-5-(trifluoromethyl)pyrimidin-4-yloxy)phenyl)acrylamide)

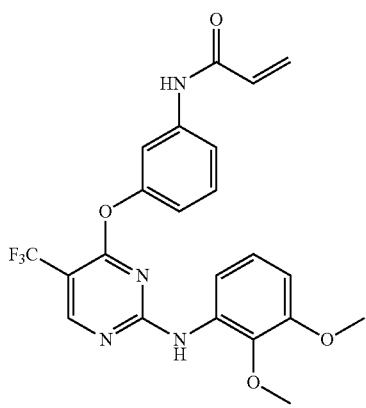 [SMILES: C=CC(=O)Nc1cccc(Oc2nc(Nc3cccc(OC)c3OC)ncc2C(F)(F)F)c1]

Compound I-23 was prepared via similar route as described in Example 1 by using N-Boc-3-aminophenol and 2,4-dichloro-5-trifluoromethylpyrimidine in Step 1 and 2,3-dimethoxyaniline in Step 4. Calculated mass for $C_{22}H_{19}F_3N_4O_4$: 460.1. found: 461.1 (M+H$^+$).

EXAMPLE 23

Compound I-17, N-(3-(5-chloro-2-(2,3-dimethoxyphenylamino)pyrimidin-4-yloxy)phenyl)acrylamide

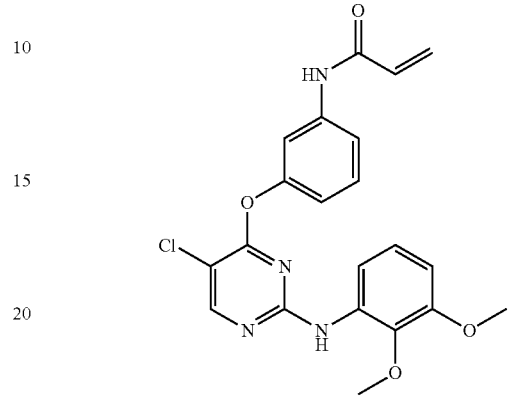

Compound I-17 was prepared via similar route as described in Example 1 by using N-Boc-3-aminophenol and 2,4,5-trichloropyrimidine in Step 1 and 2,3-dimethoxyaniline in Step 4. Calculated mass for $C_{21}H_{19}ClN_4O_4$: 426.9. found: 427.3 (M+H$^+$).

Biological Examples

Described below are assays used to measure the biological activity of provided compounds as selective inhibitors of mutant EGFR as compared to WT EGFR (and other protein kinases).

EXAMPLE 24

Omnia Assay Protocol for Potency Assessment Against EGFR (WT) and EGFR (T790M/L858R) Active Enzymes Below describes the biochemical assay protocol using EGFR-WT and EGFR-T790M/L858R.

The mechanics of the assay platform are best described by the vendor (Invitrogen, Carlsbad, Calif.) on their website at the following URL: www.invitrogen.com/content.cfm?pageid=11338 or www.invitrogen.com/site/us/en/home/Products-and-Services/Applications/Drug-Discovery/Target-and-Lead-Identification-and-Validation/KinaseBiology/KB-Misc/Biochemical-Assays/Omnia-Kinase-Assays.html.

Briefly, 10× stocks of EGFR-WT (PV3872) from Invitrogen and EGFR-T790M/L858R (40350) from BPS Bioscience, San Diego, Calif., 1.13×ATP (AS001A) and appropriate Tyr-Sox conjugated peptide substrates (KCZ1001) were prepared in 1× kinase reaction buffer consisting of 20 mM Tris, pH 7.5, 5 mM MgCl$_2$, 1 mM EGTA, 5 mM β-glycerophosphate, 5% glycerol (10× stock, KB002A) and 0.2 mM DTT (DS001A). 5 µL of each enzyme were pre-incubated in a Corning (#3574) 384-well, white, non-binding surface microtiter plate (Corning, N.Y.) for 30 min. at 25° C. with a 0.5 µL volume of 50% DMSO and serially diluted compounds prepared in 50% DMSO. Kinase reactions were started with the addition of 45 µL of the ATP/Tyr-Sox peptide substrate mix and monitored every 71 seconds for 60 minutes at $\lambda_{ex}360/\lambda_{em}485$ in a Synergy$^4$ plate reader from BioTek (Winooski, Vt.). At the conclusion of each assay, progress curves from each well were examined for linear reaction kinetics and fit statistics ($R^2$, 95% confidence interval, absolute sum of squares). Initial velocity (0 minutes to ~30 minutes) from each reaction was determined from the slope of a plot of relative fluorescence units vs time (minutes) and then plotted against inhibitor concentration to estimate $IC_{50}$ from log [Inhibitor] vs Response, Variable Slope model in GraphPad Prism from GraphPad Software (San Diego, Calif.).

[EGFR-WT]=5 nM, [ATP]=15 uM, [Y12-Sox]=5 uM (ATP $K_{Mapp}$~12 uM); and [EGFR-T790M/L858R]=2.5 nM, [ATP]=20 uM, [Y12-Sox]=5 uM (ATP $K_{Mapp}$~20 uM).

Table 3 shows the activity of selected compounds of this invention in the EGFR inhibition assay described above. Table 3 shows mutant EGFR data as compared to WT EGFR and provides the selectivity ratio of WT to mutant for each test compound. The compound numbers correspond to the compound numbers in Table 1.

TABLE 3

EGFR (Mutant and Wild Type) Biochemical Inhibition Data

| Compound # | WT EGFR $IC_{50}$ (nM) | EGFR (T790M/L858R) $IC_{50}$ (nM) | Ratio WT/mutant |
|---|---|---|---|
| I-1 | 100-300 | 1-10 | >50 |
| I-2 | 100-300 | 1-10 | >50 |
| I-3 | 10-30 | <1 | >40 |
| I-4 | 30-100 | 1-10 | >30 |
| I-5 | 30-100 | <1 | >45 |
| I-6 | 300-1000 | 10-30 | >45 |
| I-7 | 10-30 | 1-10 | >25 |
| I-8 | 30-100 | <1 | >50 |
| I-9 | 100-300 | 1-10 | >50 |
| I-10 | 30-100 | <1 | >50 |
| I-11 | 10-30 | <1 | >25 |
| I-12 | 300-1000 | <1 | >50 |
| I-13 | 30-100 | 1-10 | >25 |
| I-14 | 300-1000 | 1-10 | >50 |
| I-15 | 100-300 | 1-10 | >50 |
| I-16 | 100-300 | 1-10 | >50 |
| I-17 | 300-1000 | 10-100 | >35 |
| I-18 | 300-1000 | 10-30 | >30 |
| I-19 | 100-300 | 10-30 | >10 |
| I-20 | 30-100 | 1-10 | >45 |
| I-21 | 100-300 | 1-10 | >50 |
| I-22 | 100-300 | 1-10 | >50 |
| I-23 | >1000 | 10-30 | >50 |

EXAMPLE 25

Cell Culture and Antibodies

A431 human epidermoid carcinoma, H1975 human NSCLC and HCC827 human NSCLC adenocarcinoma cells were obtained from the American Type Culture Center (Manassas, Va.). A431 cells were grown in DMEM (Invitrogen, Carlsbad, Calif.) supplemented with 10% FBS (HyClone, South Logan, Utah) and 1% Penicillin-Streptomycin (P/S, Lonza, Walkersville, Md.). H1975 and HCC827 cells were grown in complete RPMI 1640 (Invitrogen) supplemented with 10% FBS and 1% P/S. All cells were maintained and propagated as monolayer cultures at 37° C. in a humidified 5% $CO_2$ incubator.

All primary antibodies were obtained from Cell Signaling (Danvers, Mass.) and used at 1:1000. Secondary antibodies were used at 1:10,000. Goat anti-mouse IgG IRDye 800CW antibody was obtained from LiCor Biosciences (Lincoln, Nebr.) and goat anti-rabbit IgG Alexa Fluor 680 was obtained from Invitrogen.

Immunoblotting

Cells were grown in 12-well plates (Corning, Coring, N.Y.) to 90% confluence and then incubated in low-serum (0.1% FBS) media for 16-18 hr. Cells were then treated with 5, 1.25, 0.31, 0.078, 0.020 or 0.005 μM test compound in low-serum (0.1% FBS) media for 1 hr. A431 cells were then stimulated with 50 ng/ml EGF (Peprotech, Rocky Hill, N.J.) for 15 min. After treatment, cell monolayers were washed with cold PBS (Invitrogen) and immediately lysed by scrapping into 60 uL cold Cell Extraction Buffer (Invitrogen) supplemented with Complete Protease inhibitors (Roche, Indianapolis, Ind.) and PhosphoSTOP (Roche) phosphatase inhibitors.

Lysate protein concentrations were determined by BCA Assay (Pierce, Rockford, Ill.) and 50 ug of each lysate was separated by 4-12% gradient SDS-PAGE (Invitrogen), transferred to nitrocellulose membrane (Biorad, Hercules, Calif.) and probed with specific antibodies. Phospho-protein signals were quantitated using Odyssey Infrared Imaging (Li-Cor Biosciences).

To assess phosphor-EGFR signaling, blots were probed with rabbit anti-Phospho-EGFR (Y1068) and mouse total anti-EGFR antibodies. Phospho-EGFR signal was normalized to total EGFR expression for each sample. To assess phosphor-S6 ribosomal protein signaling, blots were probed with mouse anti-phosphor-S6 ribosomal protein and rabbit total anti-S6 ribosomal protein. Blots were normalized as indicated above. Results are indicated as % DMSO control. Normalized data was fitted using a sigmoidal curve analysis program (Graph Pad Prism version 5) with variable Hill slope to determine the $EC_{50}$ values.

The results of this experiment is depicted in FIG. 1 and FIG. 2 and Table 4, where it shows that test compounds I-3 and I-7 are mutant selective by only inhibiting pEGFR and its downstream target S6 Ribosomal protein in H1975 cells, while completely WT-EGFR sparing in A431 cells.

Table 4 shows mutant EGFR data in H1975 (double mutation L858R/T790M) and HCC827 (delE746-A750 mutation) cells as compared to WT EGFR (A431 cells). The compound numbers recited in Table 4 correspond to the compound numbers in Table 1.

TABLE 4

EGFR (Mutant and Wild Type) Signaling (1 hr)

| Compound # | WT EGFR $EC_{50}$ (nM) | H1975 $EC_{50}$ (nM) | Ratio WT/mutant | HCC827 $EC_{50}$ (nM) | Ratio WT/mutant |
|---|---|---|---|---|---|
| I-1 | >1000 | 10-100 | >50 | 10-100 | >50 |
| I-2 | >1000 | 10-100 | >50 | <10 | >50 |
| I-3 | >1000 | 10-100 | >50 | 10-100 | >50 |
| I-4 | >1000 | 100-500 | >20 | — | — |
| I-5 | >1000 | 10-100 | >50 | — | — |
| I-6 | — | 10-100 | — | — | — |
| I-7 | >1000 | 10-100 | >50 | — | — |
| I-8 | >1000 | 100-500 | >5 | 500-1000 | >1 |
| I-9 | >1000 | 10-100 | >50 | — | — |
| I-10 | >1000 | 10-100 | >50 | — | — |
| I-11 | >1000 | 10-100 | >50 | 100-500 | >5 |
| I-13 | >1000 | 100-500 | >20 | — | — |
| I-14 | — | — | — | — | — |
| I-15 | >1000 | 100-500 | >10 | — | — |
| I-16 | >1000 | 100-500 | >35 | <10 | >50 |
| I-17 | — | — | — | 500-1000 | — |
| I-20 | — | 100-500 | — | — | — |
| I-21 | >1000 | 500-1000 | >5 | — | — |
| I-22 | >1000 | 100-500 | >10 | >1000 | >1 |
| I-23 | >1000 | >1000 | >1 | — | — |

EXAMPLE 26

Cell Proliferation

Cells were plated in Growth Media supplemented with 5% FBS and 1% P/S at a density of 3,000 cells per well in 96 well tissue culture plates (Corning). Cells were allowed to settle down for 4 hr and then treated with 5, 1.25, 0.31, 0.078, 0.020 or 0.005 μM test compound for 72 hr. Cell viability was determined by CellTiter Glo (Promega, Madison, Wis.) and results were converted to cell numbers using a standard curve. Growth inhibition (GI50) values were determined by Graph Pad Prism.

The result of this experiment is depicted in Table 5, where it shows mutant selective inhibition in H1975 (double mutation L858R/T790M) and HCC827 (delE746-A750 deletion mutation) cells but not in WT-EGFR A431 cells.

TABLE 5

EGFR (Mutant and Wild Type) Cell Proliferation

| Compound # | WT EGFR $GI_{50}$ (nM) | H1975 $GI_{50}$ (nM) | Ratio WT/mutant | HCC827 $GI_{50}$ (nM) | Ratio WT/mutant |
|---|---|---|---|---|---|
| I-1 | >1000 | 100-500 | >10 | 10-100 | >20 |
| I-2 | >1000 | >1000 | >1 | 100-500 | >15 |
| I-3 | >1000 | 100-500 | >5 | 10-100 | >50 |
| I-4 | >1000 | 100-500 | >20 | 100-500 | >20 |
| I-5 | >1000 | >1000 | >1 | 100-500 | >20 |
| I-6 | >1000 | 500-1000 | >1 | 500-1000 | >1 |
| I-7 | >1000 | 100-500 | >10 | 100-500 | >15 |
| I-8 | >1000 | >1000 | >1 | 100-500 | >10 |
| I-9 | >1000 | 100-500 | >10 | 100-500 | >25 |
| I-10 | >1000 | 100-500 | >10 | 100-500 | >10 |
| I-11 | >1000 | 100-500 | >10 | 10-100 | >40 |
| I-12 | >1000 | >1000 | >1 | 500-1000 | >5 |
| I-13 | >1000 | 500-1000 | >1 | 100-500 | >20 |
| I-15 | >1000 | >1000 | >1 | 100-500 | >25 |
| I-16 | >1000 | >1000 | >1 | 500-1000 | >5 |
| I-18 | >1000 | >1000 | >1 | 500-1000 | >5 |
| I-19 | >1000 | >1000 | >1 | 100-500 | >10 |
| I-20 | >1000 | >1000 | >1 | 100-500 | >10 |
| I-21 | >1000 | >1000 | >1 | 500-1000 | >5 |
| I-22 | >1000 | 500-1000 | >1 | 500-1000 | >5 |
| I-23 | >1000 | >1000 | >1 | >1000 | >1 |

EXAMPLE 27

Washout Experiment in H1975 Cells Containing EGFR Deletion/T790M Mutation

Cells were plated in Growth Media supplemented with 10% FBS and 1% P/S at a density of 2.0×10 5 cells per well in 12 well tissue culture plates. Cells were allowed to settle down for 4 hrs and then maintained in low-serum (0.1% FBS) media overnight.

The following morning the media was removed and the cells were treated with 500 nM test compound in low-serum media for 1 hr. The cells were washed free of compound 2× with PBS (Invitrogen). One set of cells were immediately lysed as indicated above as the 0 hr time point. The remaining cells were incubated with complete RPMI-1640 growth media (10% FBS) for 1, 3, 6 and 24 hr. For the first 1 hr, cells were washed 2× with PBS every 30 min. DMSO (0.5%) controls were collected at the 0, 3, 6 and 24 hr time points.

Figure 3:
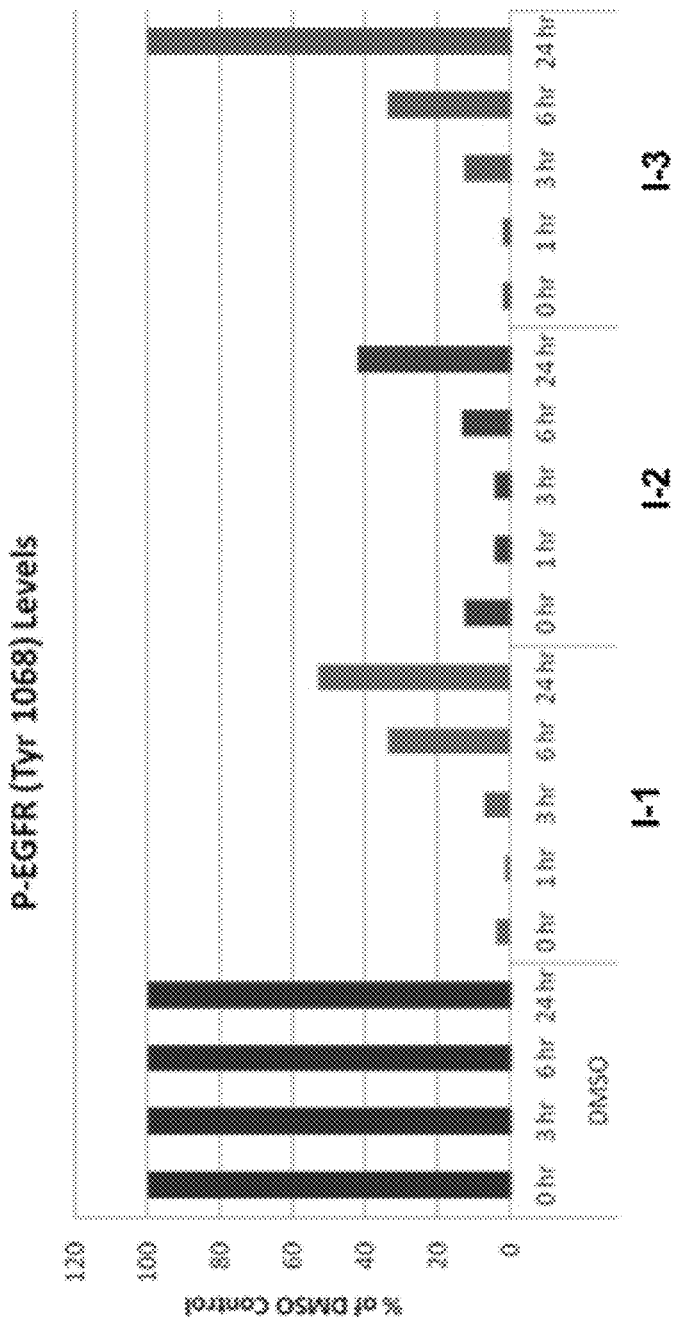
FIG. 3 depicts dose response inhibition of pEGFR with compounds I-1, I-2, and I-3 in H1975 cells in a "washout" experiment.

The results of this experiment are depicted in FIG. 3, where it shows prolonged duration of action for test compounds I-1, I-2, and I-3.

EXAMPLE 28

Mass Spectrometry for Mutant EGFR

Figure 4:
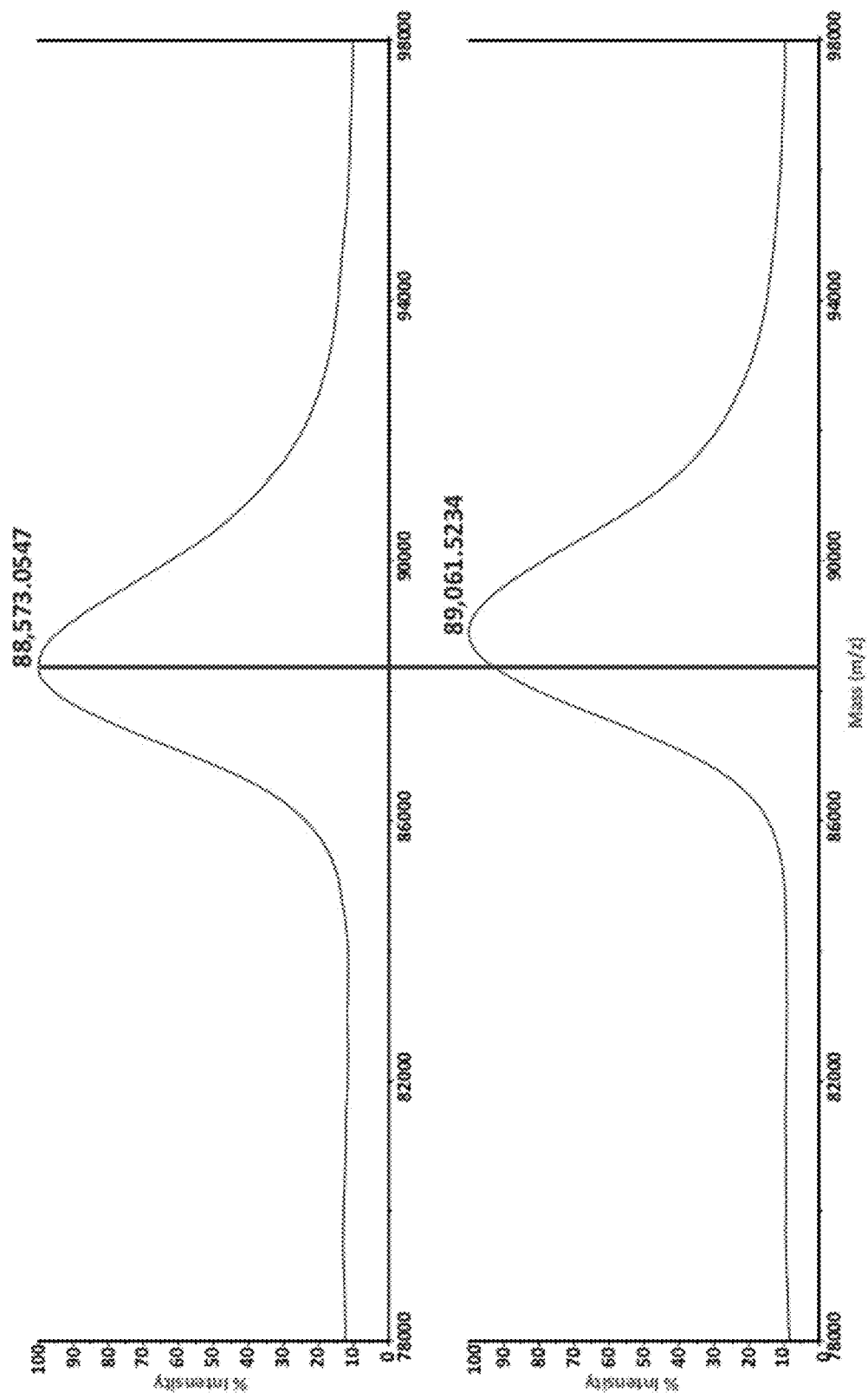
FIG. 4 depicts MS analysis confirming covalent modification of EGFR T790M/L858R by compound I-1.

Intact EGFR T790M/L858R (BPS Bioscience San Diego, Calif.) was incubated for 60 min at 37° C. with a 10-fold excess of compound I-1. 3 μL aliquots of the samples were diluted with 15 μL of 0.2% TFA prior to C4-Ziptipping directly onto the MALDI target plate using sinapinic acid as the desorption matrix (10 mg/mL in 0.1% TFA:acetonitrile, 50:50). The top panel shows the trace of the EGFR T790M/L858R protein (m/z=88,573 Da), the bottom panel shows the trace after a 30 minute incubation with I-1 (429.40 Da) with a m/z=89,061 Da. As depicted in FIG. 4, there is a mass shift of 488 Da (113%) observed, indicating that I-1 completely modifies EGFR T790M/L858R within 30 minutes.

Compounds I-2, I-3, and I-7 were similarly tested and found to covalently modify the protein.

While a number of embodiments of this invention are described herein, it is apparent that the basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

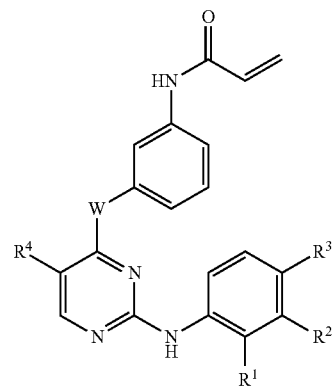

or a pharmaceutically acceptable salt thereof, wherein:
W is —O— or —NH—;
$R^1$ is —OR;
each R is independently $C_{1-4}$ alkyl or $C_{1-4}$ fluoroalkyl;
each of $R^2$ and $R^3$ is independently hydrogen, —OH, or —OR; and
$R^4$ is —$CF_3$, Cl, or Br,
wherein the compound is not

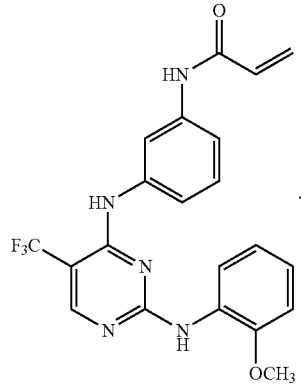 [SMILES: C=CC(=O)Nc1cccc(Nc2nc(Nc3ccccc3OC)ncc2C(F)(F)F)c1]

2. The compound according to claim 1, having at least one definition selected from (a), (b), (c), (d), or (e):

(a) W is —O—;
(b) R₁ is —OCH₃;
(c) R² is hydrogen or —OCH₃;
(d) R³ is hydrogen or —OCH₃; or
(e) R⁴ is —CF₃ or —Cl.

3. The compound according to claim 2, having at least two definitions selected from (a), (b), (c), (d), or (e).

4. The compound according to claim 3, having at least three definitions selected from (a), (b), (c), (d), or (e).

5. The compound according to claim 4, having at least four definitions selected from (a), (b), (c), (d), or (e).

6. The compound according to claim 1, having at least one definition selected from (a), (b), (c), (d), or (e):

(a) W is —NH—;
(b) R¹ is —OCH₃;
(c) R² is hydrogen or —OCH₃;
(d) R³ is hydrogen or —OCH₃; or
(e) R⁴ is —CF₃ or —Cl.

7. The compound according to claim 6, having at least two definitions selected from (a), (b), (c), (d), or (e).

8. The compound according to claim 7, having at least three definitions selected from (a), (b), (c), (d), or (e).

9. The compound according to claim 8, having at least four definitions selected from (a), (b), (c), (d), or (e).

10. The compound according to claim 1, having at least one definition selected from (a), (b), (c), (d), or (e):

(a) W is —O— or —NH—;
(b) R¹ is OCH₃;
(c) R² is hydrogen or —OCH₃;
(d) R³ is hydrogen or OCH₃; or
(e) R⁵ is —CF₃ or —Cl.

11. The compound according to claim 10, having at least two definitions selected from (a), (b), (c), (d), or (e).

12. The compound according to claim 11, having at least three definitions selected from (a), (b), (c), (d), or (e).

13. The compound according to claim 12, having at least four definitions selected from (a), (b), (c), (d), or (e).

14. The compound according to claim 1, wherein said compound is selected from:

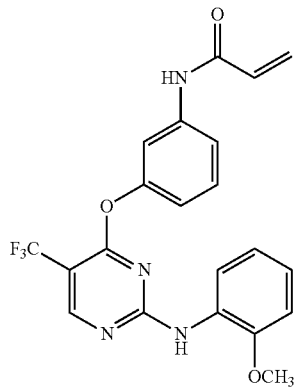

I-2

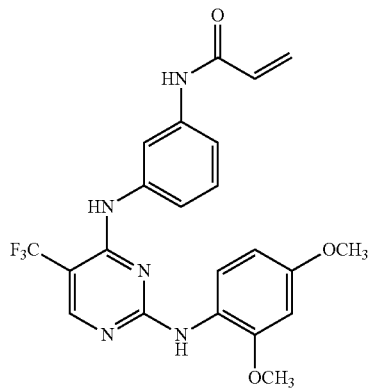

I-3

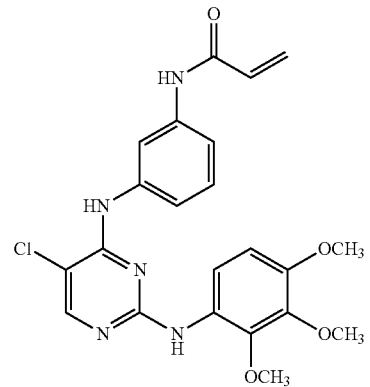

I-4

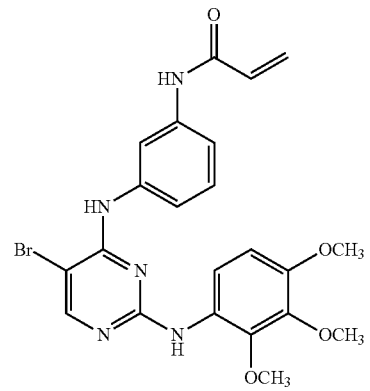

I-5

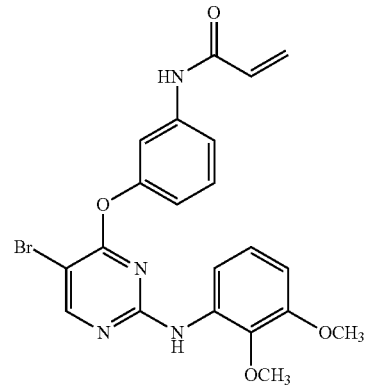

I-6

-continued
I-7
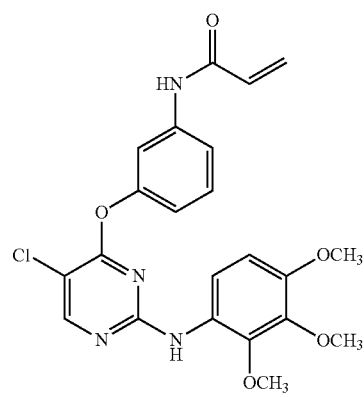
I-8
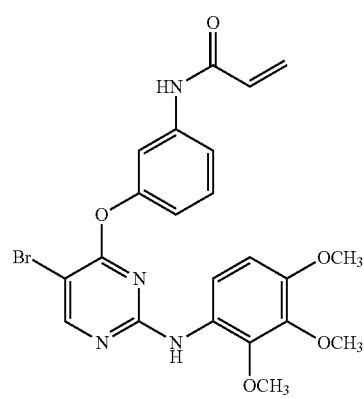
I-9
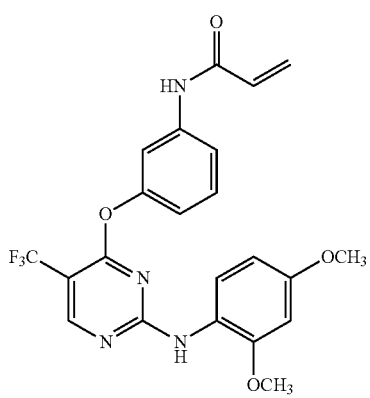
I-10
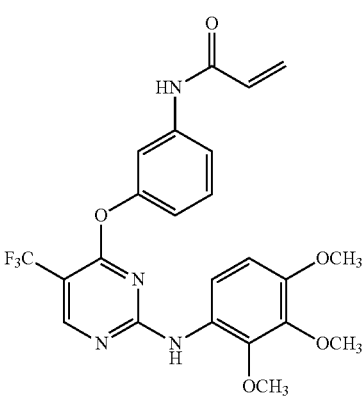
-continued
I-11
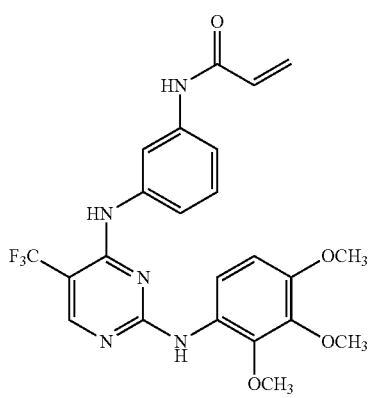
I-12
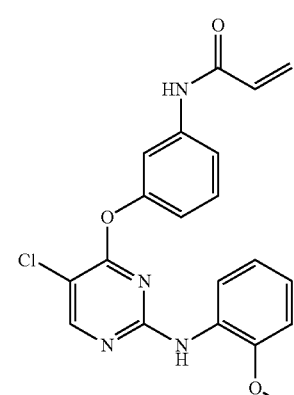
I-13
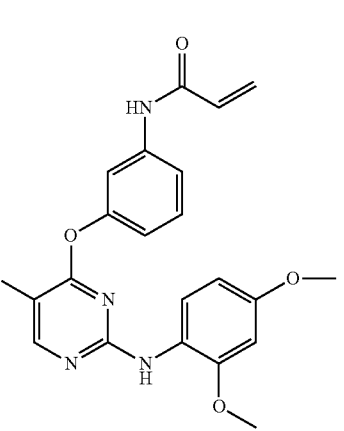
I-14
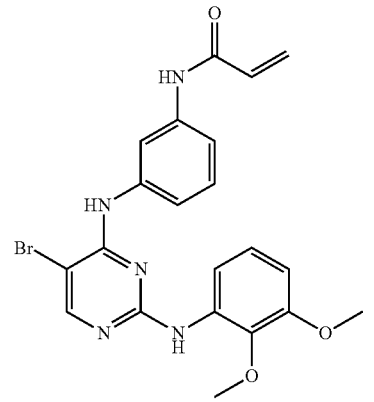

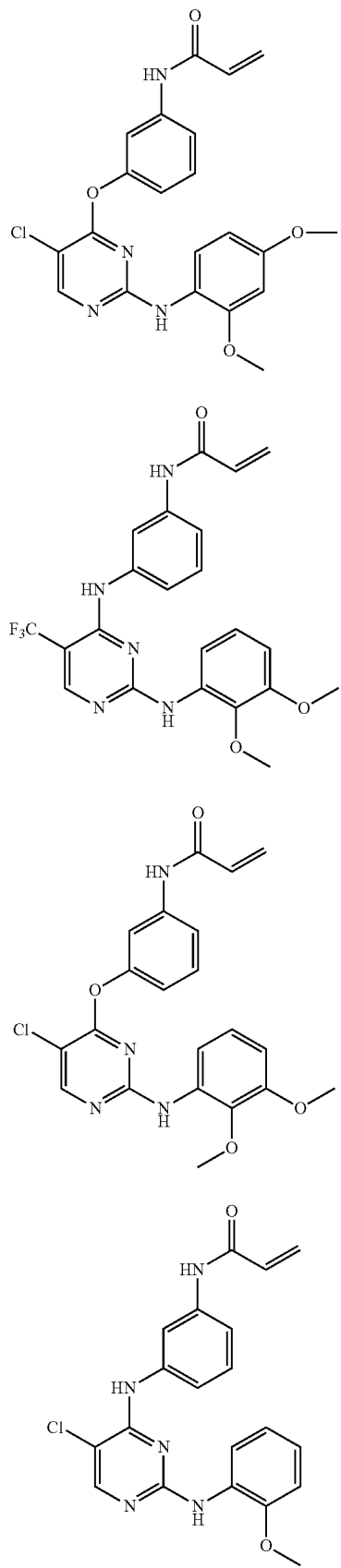
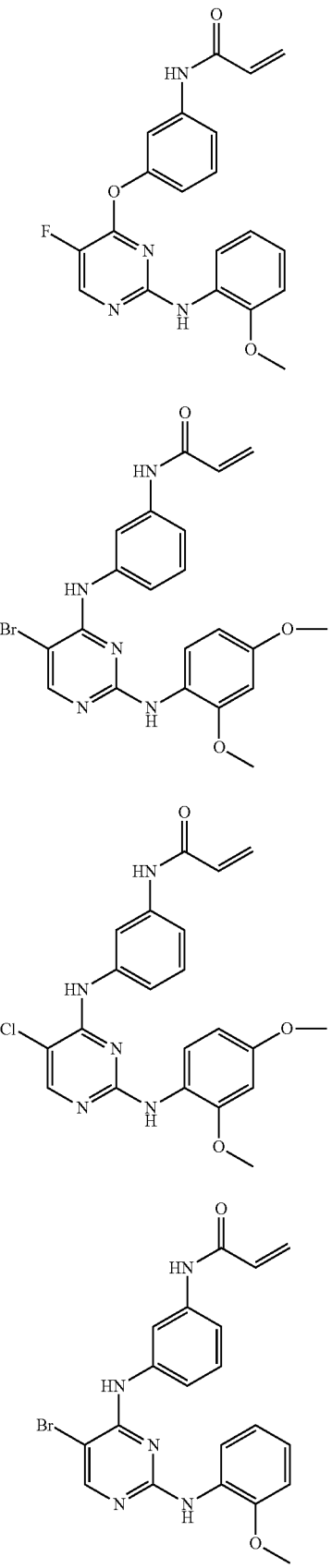

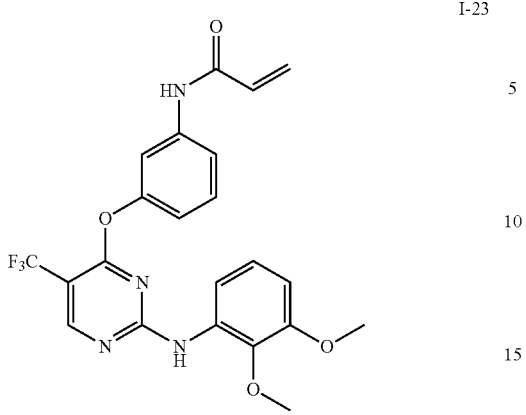

I-23 or a pharmaceutically acceptable salt thereof.

15. A composition comprising a compound according to claim 1 and a pharmaceutically acceptable carrier, adjuvant, or vehicle.

16. The composition according to claim 15, in combination with an additional therapeutic agent.

17. The composition according to claim 16, wherein the additional therapeutic agent is a chemotherapeutic agent.

* * * * *